US007119181B1

(12) United States Patent
Alizon et al.

(10) Patent No.: US 7,119,181 B1
(45) Date of Patent: Oct. 10, 2006

(54) DNA SEQUENCES AND PEPTIDES OF HUMAN IMMUNODEFICIENCY VIRUS (HIV-1)

(75) Inventors: Marc Alizon, Paris (FR); Pierre Sonigo, Paris (FR); Cole Stewart, Chatillon (FR); Oliver Danos, Paris (FR); Simon Wain-Hobson, Montigny les Bretonneux (FR)

(73) Assignees: Institut Pasteur, Paris (FR); Centre National de la Recherche Scientifique, Paris (FR)

( * ) Notice: Subject to any disclaimer, the term of this patent is extended or adjusted under 35 U.S.C. 154(b) by 0 days.

(21) Appl. No.: 08/308,218

(22) Filed: Sep. 19, 1994

Related U.S. Application Data

(60) Continuation of application No. 07/953,060, filed on Nov. 5, 1992, now abandoned, which is a division of application No. 07/158,652, filed on Feb. 22, 1988, which is a division of application No. 06/771,248, filed on Aug. 30, 1985.

(30) Foreign Application Priority Data

Oct. 18, 1984 (FR) .................................. 84 16013
Nov. 16, 1984 (GB) .................................. 84 29099

(51) Int. Cl.
*C07H 21/02* (2006.01)
*C12N 15/00* (2006.01)

(52) U.S. Cl. .................................. 536/23.1; 435/320.1

(58) Field of Classification Search .................. 536/23, 536/72; 435/5, 6; 930/221
See application file for complete search history.

(56) References Cited

U.S. PATENT DOCUMENTS

| | | | | |
|---|---|---|---|---|
| 4,520,113 A | | 5/1985 | Gallo et al. | 435/5 |
| 4,629,783 A | | 12/1986 | Cosand | 530/324 |
| 4,677,054 A | * | 6/1987 | White et al. | 435/6 |
| 4,725,669 A | | 2/1988 | Essex et al. | 530/322 |
| 5,001,230 A | * | 3/1991 | Brown et al. | 536/23.1 |
| 5,156,949 A | | 10/1992 | Luciw et al. | 435/5 |
| 5,221,610 A | * | 6/1993 | Montagnier et al. | 435/7.1 |
| 5,726,017 A | | 3/1998 | Lochrie et al. | 435/6 |
| 6,001,977 A | * | 12/1999 | Chang et al. | 530/389.4 |

FOREIGN PATENT DOCUMENTS

| | | |
|---|---|---|
| EP | 0 113 078 | 7/1984 |
| EP | 0 115 459 | 8/1984 |
| EP | 0 199 301 | 10/1986 |
| WO | WO 84/04327 | 11/1984 |
| WO | WO 91/04051 | 4/1991 |

OTHER PUBLICATIONS

B. H. Hahn et al, (1984) Nature 312: 166-169.*
B. F. Haynes (1993) Science 360: 1279-1286.*
Richterich, Peter, “Estimation of errors in ‘Raw’ DNA sequences: a validation study”, Genome Research (1998) 8:251-259.*
Crewdson, John, “Science Fictions”, 2002, pp. 165, 173, 565.*
Schupbach et al., Science, 244, 503-505 (1984).
Kalyanaraman et al., Science, 225, 321-323 (1984).
Robey etal., Science, 228: 593-595 (1985).
Allan et al., Science, 228, 1091-1094 (1985).
Crowl et al., Chemical Abstracts, 103, p. 190, No. 154983e (1985).
Montagnier et al., Chemical Abstracts, 103, p. 263, No. 34641v (1985).
Weiss et al., Nature, 316, 69-72 (1985).
Barin et al., Science, 228, 1094-1096 (1985).
Dreesman et al., Nature, 295, 158-160 (1982).
Kitchen et al., Nature, 312, 367-369 (1984).
Wain-Hobson et al., Cell, 40, 9-17 (1985).
Muesing et al., Nature, 313, 450-458 (1985).
Schneider et al., Chemical Abstracts, 103, p. 430, No. 52370k (1985).
Sarngadharan et al., Chemical Abstracts, 103, p. 551, No. 121329t (1985).
Alizon et al., Nature, 312, 757-760 (1984).
Chang et al., Nature, 315, 151-154 (1985).
Chang et al., Biotechnology, 3, 905-909 (1985).

* cited by examiner

*Primary Examiner*—Jeffrey Fredman
(74) *Attorney, Agent, or Firm*—Finnegan, Henderson, Farabow, Garrett & Dunner, LLP

(57) ABSTRACT

This invention is in the field of lymphadenopathy virus, which has been designated Human Immunodeficiency Virus Type 1 (HIV-1). This invention relates to a diagnostic means and method to detect the presence of DNA, RNA or antibodies of the lymphadenopathy retrovirus associated with the acquired immune deficiency syndrome or of the lymphadenopathy syndrome by the use of DNA fragments or the peptides encoded by said DNA fragments. The invention further relates to the DNA fragments, vectors comprising them and the proteins expressed.

13 Claims, 25 Drawing Sheets

```
ORF-R
G W Q V V K K * C G W M A Y C K G K N E T S * A S S R W G G S S I S R P G K T W
G G K W S K S S V V G W P T V R E R M R R A E P A A D G V G A A S R D L E K H G
V A S G Q K V V W L D G L L * G K E * D E L S Q Q Q M G W E Q H L E T W K N M E
GGGTGGCAAGTGGTCAAAAAGTAGTGTGGTTGGATGGCCTACTGTAAGGGAAAGAATGAGACGAGCTGAGCCAGCAGCAGATGGGGTGGGAGCAGCATCTCGAGACCTGGAAAAACATGG
8290 8300 8310 8320 8330 8340 8350 8360 8370 8380 8390 8400

PHASE 1
      2 R
      3
S N H K * Q Y S S Y Q C C L C L A R S T R G G G G G F S S H T S G T F K T N D L
A I T S S N T A A T N A A C A W L F A Q E E E E V G F P V T P Q V P L R P M T Y
Q S Q V A I Q Q L P M L L V P G * K H K R R R R W V F Q S H L R Y L * D Q * L T
AGCAATCACAAGTAGCAATACAGCAGCTACCAATGCTGCTTGTGCCTGGCTAGAAGCACAAGAGGAGGAGGAGGTGGGTTTTCCAGTCACACCTCAGGTACCTTTAAGACCAATGACTTA
8410 8420 8430 8440 8450 8460 8470 8480 8490 8500 8510 8520

R
Q G S C R S * P L F K R K G G T G R A N S L P T K T R Y P * S V D L P H T R L L
K A A V D L S H F L K E K G G L E G L I H S Q R R Q D I L D L W I Y H T Q G Y F
R Q L * I L A T F * K K R G D W K G * F T P N E D K I S L I C G S T T H K A T S
CAAGGCAGCTGTAGATCTTAGCCACTTTTTAAAAGAAAAGGGGGGACTGGAAGGGCTAATTCACTCCCAACGAAGACAAGATATCCTTGATCTGTGGATCTACCACACACAAGGCTACTT
8530 8540 8550 8560 8570 8580 8590 8600 8610 8620 8630 8640

R
P * L A E L H T R A R G Q I S T D L W M V L Q A S T S * A R * G R R G Q * R R E
P D W Q N Y T T P G P G V R Y P L T F G W C Y K L V P V E P D K V E E A N K G E N
L I G R T T H Q G Q C S D I H * P L D G A T S * Y Q L S Q I R * K R P I K E R T
CCCTGATTGGCAGAACTACACACCAGGGCCAGGGGTCAGATATCCACTGACCTTTGGATGGTGCTACAAGCTAGTACCAGTTGAGCCAGATAAGGTAGAAGAGGCCAATAAAGGAGAGAA
8650 8660 8670 8680 8690 8700 8710 8720 8730 8740 8750 8760

R
H Q L V T P C E P A W N C * P * E R S V R V E V * Q P P S I S S R G P R A A S G
T S L L H P V S L H G M D D P E R E V L E W R F D S R L A F H H V A R E L H P E
P A C Y T L * A C M E W M T L R E K C * S G G L T A A * H F I T W P E S C I R S
CACCAGCTTGTTACACCCTGTGAGCCTGCATGGAATGGATGACCCTGAGAGAGAAGTGTTAGAGTGGAGGTTTGACAGCCGCCTAGCATTTCATCACGTGGCCCGAGAGCTGCATCCGGA
8770 8780 8790 8800 8810 8820 8830 8840 8850 8860 8870 8880

R
V L Q E L L T S S L L Q G T F R W S L S R E A W P G R N W G V A S P Q M L H I S
Y F K N C * H R A C Y K G L S A G D F P G R W G L G G T G E W R A L R C C I * A
T S R T A D I E L A T R D F P L G T F Q G G V A W A E L G S G E P S D A A Y K Q
GTACTTCAAGAACTGCTGACATCGAGCTTGCTACAAGGGACTTTCCGCTGGGGACTTTCCAGGGAGGCGTGGCCTGGGCGGAACTGGGGAGTGGCGAGCCCTCAGATGCTGCATATAAGC
8890 8900 8910 8920 8930 8940 8950 8960 8970 8980 8990 9000
END-ORF-R

S C F L P V L G L S G * T R F E P G S S L A N * G T H C L S L N K
A A F C L Y W V S L V P P D L S L S A L W L I R E P T A * A S I
L L F A C T G S L W L D Q I * A W E L S G * L G N P L L K P Q
AGCTGCTTTTTGCCTGTACTGGGTCTCTCTGGTTAGACCAGATTTGAGCCTGGGAGCTCTCTGGCTAACTAGGGAACCCACTGCTTAAGCCTCAATA
9010 9020 9030 9040 9050 9060 9070 9080 9090 9100
```

FIG. 12

```
N R G E Q E M E P V D P R L E P W K H P G S Q P K
 T F E S K K W S Q * I L D * S P G S I Q E V S L
CAACAGAGGAGAGCAAGAAATGGAGCCAGTAGATCCTAGACTAGAGCCCTGGAAGCATCCAGGAAGTCAGCCTAA
    5290     5300     5310     5320     5330     5340     5350

P S L F H N K S L R H L L W Q E E A E T A T K T S
 Q V C F T T K A L G I S Y G R K K R R Q R R R P P
 K F V S Q Q K P * A S P M A G R S G D S D E D L L
CCAAGTTTGTTTCACAACAAAAGCCTTAGGCATCTCCTATGGCAGGAAGAAGCGGAGACAGCGACGAAGACCTCCT
    5410     5420     5430     5440     5450     5460     5470

S T C N A T Y T N S N S S I S S S N N N S N S C V
 V H V M Q P I Q I A I A A L V V A I I I A I V V W
 Y M * C N L Y K * Q * Q H * * * Q * * * Q * L C C
AGTACATGTAATGCAACCTATACAAATAGCAATAGCAGCATTAGTAGTAGCAATAATAATAGCAATAGTTGTGTGG
    5530     5540     5550     5560     5570     5580     5590

N R Q V N * * T N R K S R R Q W Q * E * R R N I S
 I D R L I D R L I E R A E D S G N E S E G E I S A
 * T G * L I D * * K E Q K T V A M R V K E K Y Q H
AATAGACAGGTTAATTGATAGACTAATAGAAAGAGCAGAAGACAGTGGCAATGAGAGTGAAGGAGAAATATCAGCA
    5650     5660     5670     5680     5690     5700     5710

Y * * S V V L Q K N C G S Q S I M G Y L C G R K Q
 I D D L * C Y R K I V G H S L L W G T C V E G S N
 L M I C S A T E K L W V T V Y Y G V P V W K E A T
TATTGATGATCTGTAGTGCTACAGAAAAATTGTGGGTCACAGTCTATTATGGGGTACCTGTGTGGAAGGAAGCCAAC
    5770     5780     5790     5800     5810     5820     5830

R Y I M F G P H M P V Y P Q T P T H K K * Y W * M
 G T * C L G H T C L C T H R P Q P T R S S I G K C
 V H N V W A T H A C V P T D P N P Q E V V L V N V
AGGTACATAATGTTTGGGCCACACATGCCTGTGTACCCACAGACCCCAACCCACAAGAAGTAGTATTGGTAAATGT
    5890     5900     5910     5920     5930     5940     5950

C M R I * S V Y G I K A * S H V * N * P H S V L V
 A * G Y N Q F M G S K P K A M C K I N P T L C * F
 H E D I I S L W D Q S L K P C V K L T P L C V S L
TGCATGAGGATATAATCAGTTTATGGGATCAAAGCCTAAAGCCATGTGTAAAATTAACCCCACTCTGTGTTAGTTT
    6010     6020     6030     6040     6050     6060     6070

I P I V V A G K * * W R K E R * K T A L S I S A Q
 Y Q * * * R G N D D G E R R D K K L L F Q Y Q H K
 T N S S S G E M M M E K G E I K N C S F N I S T S
ATACCAATAGTAGTAGCGGGGAAAATGATGATGGAGAAAGGAGAGATAAAAAACTGCTCTTTCAATATCAGCACAAG
    6130     6140     6150     6160     6170     6180     6190

L I * Y Q * I M I L P A I R * Q V V T P Q S L H R
 * Y N T N R * * Y Y Q L Y V D K L * H L S H Y T G
 D I I P I D N D T T S Y T L T S C N T S V I T Q A
TTGATATAATACCAATAGATAATGATACTACCAGCTATACGTTCACAAGTTGTAACACCTCAGTCATTACACAGGG
    6250     6260     6270     6280     6290     6300     6310

P R L V L R P * N V I I R R S M E Q D H V Q M S A
```

```
P  G  S  Q  P  K  T  A  C  I  T  C  Y  C  K  K  C  C  F  H  C
 Q  E  V  S  L  K  L  L  V  P  L  A  I  V  K  S  V  A  F  I  A
CAGGAAGTCAGCCTAAAACTGCTTGTACCACTTGCTATTGTAAAAAGTGTTGCTTTCATTG
        5350      5360      5370      5380      5390      5400

 A  T  K  T  S  S  R  Q  S  D  S  S  S  F  S  I  K  A  V  S
Q  R  R  R  P  P  Q  G  S  Q  T  H  Q  V  S  L  S  K  Q  *  V
 S  D  E  D  L  L  K  A  V  R  L  I  K  F  L  Y  Q  S  S  K  *
AGCGACGAAGACCTCCTCAAGGCAGTCAGACTCATCAAGTTTCTCTATCAAAGCAGTAAGT
        5470      5480      5490      5500      5510      5520

 S  N  S  C  V  V  H  S  N  H  R  I  *  E  N  I  K  T  K  K
I  A  I  V  V  W  S  I  V  I  I  E  Y  R  K  I  L  R  Q  R  K
 *  Q  *  L  C  G  P  *  *  S  *  N  I  G  K  Y  *  D  K  E  K
TAGCAATAGTTGTGTGGTCCATAGTAATCATAGAATATAGGAAAATATTAAGACAAAGAAA
        5590      5600      5610      5620      5630      5640

R  R  N  I  S  T  C  G  D  G  G  G  N  G  A  P  C  S  L  G
 G  E  I  S  A  L  V  E  M  G  V  E  M  G  H  H  A  P  W  D
 K  E  K  Y  Q  H  L  W  R  W  G  W  K  W  G  T  M  L  L  G  I
AAGGAGAAATATCAGCACTTGTGGAGATGGGGGTGGAAATGGGGCACCATGCTCCTTGGGA

        5710      5720      5730      5740      5750      5760

C  G  P  K  Q  P  P  L  Y  F  V  H  Q  M  L  K  H  M  I  Q
 V  E  G  S  N  H  H  S  I  L  C  I  R  C  *  S  I  *  Y  R
V  W  K  E  A  T  T  T  L  F  C  A  S  D  A  K  A  Y  D  T  E
TGTGGAAGGAAGCAACCACCACTCTATTTTGTGCATCAGATGCTAAAGCATATGATACAG
       5830      5840      5850      5860      5870      5880

 *  Y  W  *  M  *  Q  K  I  L  T  C  G  K  M  T  W  *  N  R
 S  I  G  K  C  D  R  K  F  *  H  V  E  K  *  H  G  R  T  D
V  V  L  V [N  V  T] E  N  F  N  M  W  K  N  D  M  V  E  Q  M
TAGTATTGGTAAATGTGACAGAAAATTTTAACATGTGGAAAAATGACATGGTAGAACAGA
       5950      5960      5970      5980      5990      6000

H  S  V  L  V  *  S  A  L  I  W  G  M  L  L  I  P  I  V  V
 T  L  C  *  F  K  V  H  *  F  G  E  C  Y  *  Y  Q  *  *  *
P  L  C  V  S  L  K  C  T  D  L  G [N  A  T] N  T [N  S  S] N
CACTCTGTGTTAGTTTAAAGTGCACTGATTTGGGGAATGCTACTAATACCAATAGTAGTA
       6070      6080      6090      6100      6110      6120

S  I  S  A  Q  A  *  E  V  R  C  R  K  N  M  H  F  F  I  N
 Q  Y  Q  H  K  K  H  K  R  *  G  A  E  R  I  C  I  F  L  *  T
F [N  I  S] T  S  I  R  G  K  V  Q  K  E  Y  A  F  F  Y  K  L
TCAATATCAGCACAAGCATAAGAGGTAAGGTGCAGAAAGAATATGCATTTTTTATAAAC
       6190      6200      6210      6220      6230      6240

Q  S  L  H  R  P  V  Q  R  Y  P  L  S  Q  F  P  Y  I  I  V
 S  H  Y  T  G  L  S  K  G  I  L  *  A  N  S  H  T  L  L  C
S  V  I  T  Q  A  C  P  K  V  S  F  E  P  I  P  I  H  Y  C  A
CAGTCATTACACAGGCCTGTCCAAAGGTATCCTTTGAGCCAATTCCCATACATTATTGTG
       6310      6320      6330      6340      6350      6360

V  Q  M  S  A  Q  Y  N  V  H  M  E  L  G  Q  *  Y  Q  L  N
```

```
P C W F C D S K M * * * D V Q W N R T M Y K C Q
 P A G F A I L R C N N K T F N G T G P C T N V S
CCCCGGCTGGTTTTGCGATTCTAAAATGTAATAATAAGACGTTCAATGGAACAGGACCATGTACAAATGTCAGC
   6370      6380      6390      6400      6410      6420      6430

C C * M A V * Q K K R * * L D L P I S Q T M L K P
 A V E W Q S S R R R G S N * I C Q F H R Q C * N H
  L L N G S L A E E E V V I R S A N F T D N A K T
TGCTGTTGAATGGCAGTCTAGCAGAAGAAGAGGTAGTAATTAGATCTGCCAATTTCACAGACAATGCTAAAACCA
   6490      6500      6510      6520      6530      6540      6550

P T T I Q E K V S V S R G D Q G E H L L Q * E K *
 Q Q Q Y K K K Y P Y P E G T R E S I C Y N R K N R
  N N N T R K S I R I Q R G P G R A F V T I G K I
CCAACAACAATACAAGAAAAAGTATCCGTATCCAGAGGGGACCAGGGAGAGCATTTGTTACAATAGGAAAAATAG
   6610      6620      6630      6640      6650      6660      6670

M P L * N R * L A N * E N N L E I I K Q * S L S N
 C H F K T D S * Q I K R T I W K * * N N N L * A I
  A T L K Q I A S K L R E Q F G N N K I I I F K Q
ATGCCACTTTAAAACAGATAGCTAGCAAATTAAGAGAACAATTTGGAAATAATAAAACAATAATCTTTAAGCAA
   6730      6740      6750      6760      6770      6780      6790

E G N F S T V I Q H N C L I V L G L I V L G V L K
 R G I F L L * F N T T V * * Y L V * * Y L E Y * R
  G E F F Y C N S T Q L F N S T W F N S T W S T E
GAGGGGAATTTTTCTACTGTAATTCAACACAACTGTTTAATAGTACTTGGTTTAATAGTACTTGGAGTACTGAAG
   6850      6860      6870      6880      6890      6900      6910

E * N N L * T C G R K * E K Q C M P L P S A D K L
 N K T I Y K H V A G S R K S N V C P S H Q R T N *
  I K Q F I N M W Q E V G K A M Y A P P I S G Q I
GAATAAAACAATTTATAAACATGTGGCAGGAAGTAGGAAAAGCAATGTATGCCCCTCCCATCAGCGGACAAATTA
   6970      6980      6990      7000      7010      7020      7030

V I T T M G P R S S D L E E E I * G T I G E V N Y
 * * Q Q W V R D L Q T W R R R Y E G Q L E K * I I
  N N N N G S E I F R P G G G D M R D N W R S E L
GTAATAACAACAATGGGTCCGAGATCTTCAGACCTGGAGGAGGAGATATGAGGGACAATTGGAGAAGTGAATTAT
   7090      7100      7110      7120      7130      7140      7150

P R Q R E E W C R E K K E Q W E * E L C S L G S W
 Q G K E K S G A E R K K S S G N R S F V P W V L G
  K A K R R V V Q R E K R A V G I G A L F L G F L
CCAAGGCAAAGAGAAGAGTGGTGCAGAGAGAAAAAAGAGCAGTGGGAATAGGAGCTTTGTTCCTTGGGTTCTTGG
   7210      7220      7230      7240      7250      7260      7270

Y R P D N Y C L V * C S S R T I C * G L L R R N S
 T G Q T I I V W Y S A A A E Q F A E G Y * G A T A
  Q A R Q L L S G I V Q Q Q N N L L R A I E A Q Q
TACAGGCCAGACAATTATTGTCTGGTATAGTGCAGCAGCAGAACAATTTGCTGAGGGCTATTGAGGCGCAACAGC
   7330      7340      7350      7360      7370      7380      7390

E S W L W K D T * R I N S S W G F G V A L E N S F
```

N R T M Y K C Q H S T M Y T W N * N S S I N S T
T G P C T N V S T V Q C T H G I R P V V S T Q L
AACAGGACCATGTACAAATGTCAGCACAGTACAATGTACACATGGAATTAGGCCAGTAGTATCAACTCAAC
6420 6430 6440 6450 6460 6470 6480

P I S Q T M L K P * * Y S * T N L * K L I V Q D
Q F H R Q C * N H N S T A E P I C R N * L Y K T
N F T D N A K T I I V Q L N Q S V E I N C T R P
CAATTTCACAGACAATGCTAAAACCATAATAGTACAGCTGAACCAATCTGTAGAAATTAATTGTACAAGAC
6540 6550 6560 6570 6580 6590 6600

F H L L Q * E K * E I * D K H I V T L V E Q N G
S I C Y N R K N R K Y E T S T K * H * * S K M E
A F V T I G K I G N M R Q A H C N I S R A K W N
AGCATTTGTTACAATAGGAAAAATAGGAAATATGAGACAAGCACATTGTAACATTAGTAGAGCAAAATGGA
6660 6670 6680 6690 6700 6710 6720

I I K Q * S L S N P Q E G T Q K L * R T V L I V
* * N N N L * A I L R R G P R N C N A Q F * L W
N K I I I F K Q S S G G D P E I V T H S F N C G
TAATAAAACAATAATCTTTAAGCAATCCTCAGGAGGGGACCCAGAAATTGTAACGCACAGTTTTAATTGTG
6780 6790 6800 6810 6820 6830 6840

C L I V L G V L K G Q I T L K E V T Q S H S H A
V * * Y L E Y * R V K * H * R K * H N H T P M Q
P N S T W S T E G S N N T E G S D T I T L P C R
TTTTAATAGTACTTGGAGTACTGAAGGGTCAAATAACACTGAAGGAAGTGACACAATCACACTCCCATGCA
6900 6910 6920 6930 6940 6950 6960

M P L P S A D K L D V H Q I L Q G C Y * Q E M V
C P S H Q R T N * M F I K Y Y R A A I N K R W W
A P P I S G Q I R C S S N I T G L L L T R D G G
TGCCCCTCCCATCAGCGGACAAATTAGATGTTCATCAAATATTACAGGGCTGCTATTAACAAGAGATGGTG
7020 7030 7040 7050 7060 7070 7080

* G T I G E V N Y I N I K * * K L N H * E * H P
E G Q L E K * I I * I * S S K N * T I R S S T H
R D N W R S E L Y K Y K V V K I E P L G V A P T
GAGGGACAATTGGAGAAGTGAATTATATAAATATAAAGTAGTAAAAATTGAACCATTAGGAGTAGCACCCA
7140 7150 7160 7170 7180 7190 7200

* E L C S L G S W E Q Q E A L W A H G Q * R * R
R S F V P W V L G S S R K H Y G R T V N D A D G
G A L F L G F L G A A G S T M G A R S M T L T V
AGGAGCTTTGTTCCTTGGGTTCTTGGGAGCAGCAGGAAGCACTATGGGCGCACGGTCAATGACGCTGACGG
7260 7270 7280 7290 7300 7310 7320

C * G L L R R N S I C C N S Q S G A S S S S R Q
A E G Y * G A T A S V A T H S L G H Q A A P G K
L R A I E A Q Q H L L Q L T V W G I K Q L Q A R
GCTGAGGGCTATTGAGGCGCAACAGCATCTGTTGCAACTCACAGTCTGGGGCATCAAGCAGCTCCAGGCAA
7380 7390 7400 7410 7420 7430 7440

```
 N  P  G  C  G  K  I  P  K  G  S  T  A  P  G  D  L  G  L  L  W  K  T  H
  I  L  A  V  E  R  Y  L  K  D  Q  Q  L  L  G  I  W  G  C  S  G  K  L  I
GAATCCTGGCTGTGGAAAGATACCTAAAGGATCAACAGCTCCTGGGGATTTGGGGTTGCTCTGGAAAACTCATI
      7450      7460      7470      7480      7490      7500      7510

 W  N  R  F  G  I  T  *  P  G  W  S  G  T  E  K  L  T  I  T  Q  A  *  Y  I
  G  T  D  L  E  *  H  D  L  D  G  V  G  Q  R  N  *  Q  L  H  K  L  N  T
   E  Q  I  W  N [N  M  T] W  M  E  W  D  R  E  I  N [N  Y  T] S  L  I  H
TGGAACAGATTTGGAATAACATGACCTGGATGGAGTGGGACAGAGAAATTAACAATTACACAAGCTTAATACAT
      7570      7580      7590      7600      7610      7620      7630

 N  Y  W  N  *  I  N  G  Q  V  C  S  I  G  L  T  *  Q  I  G  C  G  I  *  K
  I  I  G  I  R  *  M  G  K  F  V  E  L  V  *  H  N  K  L  A  V  V  Y  K
   L  L  E  L  D  K  W  A  S  L  W  N  W  F [N  I  T] N  W  L  W  Y  I  K
AATTATTGGAATTAGATAAATGGGCAAGTTTGTGGAATTGGTTTAACATAACAAATTGGCTGTGGTATATAAAA
      7690      7700      7710      7720      7730      7740      7750

 L  L  Y  F  L  *  *  I  E  L  G  R  D  I  H  H  Y  R  F  R  P  T  S  Q  P
  C  C  T  F  Y  S  E  *  S  *  A  G  I  F  T  I  I  V  S  D  P  P  P  N
   A  V  L  S  I  V  N  R  V  R  Q  G  Y  S  P  L  S  F  Q  T  H  L  P  T
TTGCTGTACTTTCTATAGTGAATAGAGTTAGGCAGGGATATTCACCATTATCGTTTCAGACCCACCTCCCAACC
      7810      7820      7830      7840      7850      7860      7870

 R  E  T  E  T  D  P  F  D  *  *  T  D  P  *  H  L  S  G  T  I  C  G  A  L
  E  R  Q  R  Q  I  H  S  I  S  E  R  I  L  S  T  Y  L  G  R  S  A  E  P
   R  D  R  D  R  S  I  R  L  V [N  G  S] L  A  L  I  W  D  D  L  R  S  L
AGAGAGACAGAGACAGATCCATTCGATTAGTGAACGGATCCTTAGCACTTATCTGGGACGATCTGCGGAGCCTT
      7930      7940      7950      7960      7970      7980      7990

 T  R  I  V  E  L  L  G  R  R  G  W  E  A  L  K  Y  W  W  N  L  L  Q  Y  W
  R  G  L  W  N  F  W  D  A  G  G  G  K  P  S  N  I  G  G  I  S  Y  S  I
   E  D  C  G  T  S  G  T  Q  G  V  G  S  P  Q  I  L  V  E  S  P  T  V  L
ACGAGGATTGTGGAACTTCTGGGACGCAGGGGGTGGGAAGCCCTCAAATATTGGTGGAATCTCCTACAGTATTC
      8050      8060      8070      8080      8090      8100      8110

 A  I  A  V  A  E  G  T  D  R  V  I  E  V  V  Q  G  A  C  R  A  I  R  H  I
  P  *  Q  *  L  R  G  Q  I  G  L  *  K  *  Y  K  E  L  V  E  L  F  A  T
   H  S  S  S  *  G  D  R  *  G  Y  R  S  S  T  R  S  L  *  S  Y  S  P  H
GCCATAGCAGTAGCTGAGGGGACAGATAGGGTTATAGAAGTAGTACAAGGAGCTTGTAGAGCTATTCGCCACAT
      8170      8180      8190      8200      8210      8220      8230

 G  W  Q  V  V  K  K  *  C  G  W  M  A  Y  C  K  G  K  N  E  T  S  *  A  S
  G  G  K  W  S  K  S  S  V  V  G  W  P  T  V  R  E  R  M  R  R  A  E  P
   V  A  S  G  Q  K  V  V  W  L  D  G  L  L  *  G  K  E  *  D  E  L  S  Q
GGGTGGCAAGTGGTCAAAAAGTAGTGTGGTTGGATGGCCTACTGTAAGGGAAAGAATGAGACGAGCTGAGCCAG
      8290      8300      8310      8320      8330      8340      8350

 S  N  H  K  *  Q  Y  S  S  Y  Q  C  C  L  C  L  A  R  S  T  R  G  G  G  G
  A  I  T  S  S  N  T  A  A  T  N  A  A  C  A  W  L  F  A  Q  E  E  E  E
   Q  S  Q  V  A  I  Q  Q  L  P  M  L  L  V  P  G  *  K  H  K  R  R  R  R
AGCAATCACAAGTAGCAATACAGCAGCTACCAATGCTGCTTGTGCCTGGCTAGAAGCACAAGAGGAGGAGGAGG
      8410      8420      8430      8440      8450      8460      8470

 D  G  S  C  R  S  *  P  L  F  K  R  K  G  G  T  G  R  A  N  S  L  P  I  K
```

```
W K T H L H H C C A L E C * L E * * I S
 G K L I C T T A V P W N A S W S N K S L
CTGGAAAACTCATTTGCACCACTGCTGTGCCTTGGAATGCTAGTTGGAGTAATAAATCTC
     7510      7520      7530      7540      7550      7560

Q A * Y I P * L K N R K T S K K R M N K
 K L N T F L N * R I A K P A R K E * T R
  S L I H S L I E E S Q N Q Q E K N E Q E
CAAGCTTAATACATTCCTTAATTGAAGAATCGCAAAACCAGCAAGAAAAGAATGAACAAG
     7630      7640      7650      7660      7670      7680

C G I * K Y S * * * * E A W * V * E * F
 V V Y K N I H N D S R R L G R F K N S F
  W Y I K I F I M I V G G L V G L R I V F
TGTGGTATATAAAAATATTCATAATGATAGTAGGAGGCTTGGTAGGTTTAAGAATAGTTT
     7750      7760      7770      7780      7790      7800

P T S Q P R G D P T G P K E * K K K V E
 P P P N P E G T R Q A R R N R R R R W R
  H L P T P R G P D R P E G I E E E G G E
CCACCTCCCAACCCCGAGGGACCCGACAGGCCCGAAGGAATAGAAGAAGAAGGTGGAG
     7870      7880      7890      7900      7910      7920

I C G A L C L F S Y H R L R D L L L I V
 S A E P C A S S S A T T A * E T Y S * L *
  L R S L V P L Q L P P L E R L T L D C N
TCTGCGGAGCCTTGTGCCTCTTCAGCTACCACCGCTTGAGAGACTTACTCTTGATTGTA
     7990      8000      8010      8020      8030      8040

L L Q Y W S Q E L K N S A V S L L N A T
 S Y S I G V R N * R I V L L A C S M P Q
  P T V L E S G T K E * C C * L A Q C H S
TCCTACAGTATTGGAGTCAGGAACTAAAGAATAGTGCTGTTAGCTTGCTCAATGCCACA
     8110      8120      8130      8140      8150      8160

A I R H I P R R I R Q G L E R I L L * D
 L F A T Y L E E * D R A W K G F C Y K M
  Y S P H T * K N K T G L G K D F A I R W
CTATTCGCCACATACCTAGAAGAATAAGACAGGGCTTGGAAAGGATTTTGCTATAAGAT
     8230      8240      8250      8260      8270      8280

T S * A S S R W G G S S I S R P G K T W
 R A E P A A D G V G A A S R D L E K H G
  E L S Q Q Q M G W E Q H L E T W K N M E
CGAGCTGAGCCAGCAGCAGATGGGGTGGGAGCAGCATCTCGAGACCTGGAAAAACATGG
     8350      8360      8370      8380      8390      8400

Q G G G G G F S S H T S G T F K T N D L
 E E E E V G F P V T P Q V P L R P M T Y
  R R R R R W V F Q S H L R Y L * D Q * L T
GAGGAGGAGGAGGTGGGTTTCCAGTCACACCTCAGGTACCTTTAAGACCAATGACTTA
     8470      8480      8490      8500      8510      8520

 L P T K T R Y P * S V D L P H T R L L
```

```
        10         20         30         40         50         60
AAGCTTGCCT TGAGTGCTTC AAGTAGTGTG TGCCCGTCTG TTGTGTGACT CTGGTAACTA
        70         80         90        100        110        120
GAGATCCCTC AGACCCTTTT AGTCAGTGTG GAAAATCTCT AGCAGTGGCG CCCGAACAGG
       130        140        150        160        170        180
GACTTGAAAG CGAAAGGGAA ACCAGAGGAG CTCTCTCGAC GCAGGACTCG GCTTGCTGAA
       190        200        210        220        230        240
GCGCGCACGG CAAGAGGCGA GGGGAGGCGA CTGGTGAGTA CGCCAAAAAT TTTGACTAGC
       250        260        270        280        290        300
GGAGGCTAGA AGGAGAGAGA TGGGTGCGAG AGCGTCAGTA TTAAGCGGGG GAGAATTAGA
       310        320        330        340        350        360
TCGATCGGAA AAAATTCGGT TAAGGCCAGG GGCAAAGAAA AAATATAAAT TAAAACATAT
       370        380        390        400        410        420
AGTATGGGCA AGCAGGGAGC TAGAACGATT CGCTGTTAAT CCTGGCCTGT TAGAAACATC
       430        440        450        460        470        480
AGAAGGCTGT AGACAAATAC TGGGACAGCT ACAACCATCC CTTCAGACAG GATCAGAAGA
       490        500        510        520        530        540
ACTTAGATCA TTATATAATA CAGTAGCAAC CCTCTATTGT GTGCATCAAA GGATAGAGAT
       550        560        570        580        590        600
AAAAGACACC AAGGAAGCTT TAGACAAGAT AGAGGAAGAG CAAAACAAAA GTAAGAAAAA
       610        620        630        640        650        660
AGCACAGCAA GCAGCAGCTG ACACAGGACA CAGCAGCCAG GTCAGCCAAA ATTACCCTAT
       670        680        690        700        710        720
AGTGCAGAAC ATCCAGGGGC AAATGGTACA TCAGGCCATA TCACCTAGAA CTTTAAATGC
       730        740        750        760        770        780
ATGGGTAAAA GTAGTAGAAG AGAAGGCTTT CAGCCCAGAA GTGATACCCA TGTTTTCAGC
       790        800        810        820        830        840
ATTATCAGAA GGAGCCACCC CACAAGATTT AAACACCATG CTAAACACAG TGGGGGGACA
       850        860        870        880        890        900
TCAAGCAGCC ATGCAAATGT TAAAAGAGAC CATCAATGAG GAAGCTGCAG AATGGGATAG
       910        920        930        940        950        960
AGTGCATCCA GTGCATGCAG GGCCTATTGC ACCAGGCCAG ATGAGAGAAC CAAGGGGAAG
       970        980        990       1000       1010       1020
TGACATAGCA GGAACTACTA GTACCCTTCA GGAACAAATA GGATGGATGA CAAATAATCC
      1030       1040       1050       1060       1070       1080
ACCTATCCCA GTAGGAGAAA TTTATAAAAG ATGGATAATC CTGGGATTAA ATAAAATAGT
      1090       1100       1110       1120       1130       1140
```

*FIG. 19*

```
AAGAATGTAT AGCCCTACCA GCATTCTGGA CATAAGACAA GGACCAAAAG AACCCTTTAG
      1150       1160       1170       1180       1190       1200
AGACTATGTA GACCGGTTCT ATAAAACTCT AAGAGCCGAG CAAGCTTCAC AGGAGGTAAA
      1210       1220       1230       1240       1250       1260
AAATTGGATG ACAGAAACCT TGTTGGTCCA AAATGCGAAC CCAGATTGTA AGACTATTTT
      1270       1280       1290       1300       1310       1320
AAAAGCATTG GGACCAGCAG CTACACTAGA AGAAATGATG ACAGCATGTC AGGGAGTGGG
      1330       1340       1350       1360       1370       1380
AGGACCCGGC CATAAGGCAA GAGTTTTGGC TGAAGCAATG AGCCAAGTAA CAAATTCAGC
      1390       1400       1410       1420       1430       1440
TACCATAATG ATGCAAAGAG GCAATTTTAG GAACCAAAGA AAGATTGTTA AGTGTTTCAA
      1450       1460       1470       1480       1490       1500
TTGTGGCAAA GAAGGGCACA TAGCCAGAAA TTGCAGGGCC CCTAGGAAAA AGGGCTGTTG
      1510       1520       1530       1540       1550       1560
GAAATGTGGA AAGGAAGGAC ACCAAATGAA AGATTGTACT GAGAGACAGG CTAATTTTTT
      1570       1580       1590       1600       1610       1620
AGGGAAGATC TGGCCTTCCT ACAAGGGAAG GCCAGGGAAT TTTCTTCAGA GCAGACCAGA
      1630       1640       1650       1660       1670       1680
GCCAACAGCC CCACCAGAAG AGAGCTTCAG GTCTGGGGTA GAGACAACAA CTCCCTCTCA
      1690       1700       1710       1720       1730       1740
GAAGCAGGAG CCGATAGACA AGGAACTGTA TCCTTTAACT TCCCTCAGAT CACTCTTTGG
      1750       1760       1770       1780       1790       1800
CAACGACCCC TCGTCACAAT AAAGATAGGG GGGCAACTAA AGGAAGCTCT ATTAGATACA
      1810       1820       1830       1840       1850       1860
GGAGCAGATG ATACAGTATT AGAAGAAATG AGTTTGCCAG GAAGATGGAA ACCAAAAATG
      1870       1880       1890       1900       1910       1920
ATAGGGGGAA TTGGAGGTTT TATCAAAGTA AGACAGTATG ATCAGATACT CATAGAAATC
      1930       1940       1950       1960       1970       1980
TGTGGACATA AAGCTATAGG TACAGTATTA GTAGGACCTA CACCTGTCAA CATAATTGGA
      1990       2000       2010       2020       2030       2040
AGAAATCTGT TGACTCAGAT TGGTTGCACT TTAAATTTTC CCATTAGTCC TATTGAAACT
      2050       2060       2070       2080       2090       2100
GTACCAGTAA AATTAAAGCC AGGAATGGAT GGCCCAAAAG TTAAACAATG GCCATTGACA
      2110       2120       2130       2140       2150       2160
GAAGAAAAAA TAAAAGCATT AGTAGAAATT TGTACAGAAA TGGAAAAGGA AGGGAAAATT
      2170       2180       2190       2200       2210       2220
TCAAAAATTG GGCCTGAAAA TCCATACAAT ACTCCAGTAT TTGCCATAAA GAAAAAAGAC
      2230       2240       2250       2260       2270       2280
AGTACTAAAT GGAGAAAATT AGTAGATTTC AGAGAACTTA ATAAGAGAAC TCAAGACTTC
      2290       2300       2310       2320       2330       2340
TGGGAAGTTC AATTAGGAAT ACCACATCCC GCAGGGTTAA AAAAGAAAAA ATCAGTAACA
      2350       2360       2370       2380       2390       2400
```

*FIG. 20*

```
GTACTGGATG TGGGTGATGC ATATTTTTCA GTTCCCTTAG ATGAAGACTT CAGGAAGTAT
      2410       2420       2430       2440       2450       2460
ACTGCATTTA CCATACCTAG TATAAACAAT GAGACACCAG GGATTAGATA TCAGTACAAT
      2470       2480       2490       2500       2510       2520
GTGCTTCCAC AGGGATGGAA AGGATCACCA GCAATATTCC AAAGTAGCAT GACAAAAATC
      2530       2540       2550       2560       2570       2580
TTAGAGCCTT TTAGAAAACA AAATCCAGAC ATAGTTATCT ATCAATACAT GGATGATTTG
      2590       2600       2610       2620       2630       2640
TATGTAGGAT CTGACTTAGA AATAGGGCAG CATAGAACAA AAATAGAGGA GCTGAGACAA
      2650       2660       2670       2680       2690       2700
CATCTGTTGA GGTGGGGACT TACCACACCA GACAAAAAAC ATCAGAAAGA ACCTCCATTC
      2710       2720       2730       2740       2750       2760
CTTTGGATGG GTTATGAACT CCATCCTGAT AAATGGACAG TACAGCCTAT AGTGCTGCCA
      2770       2780       2790       2800       2810       2820
GAAAAAGACA GCTGGACTGT CAATGACATA CAGAAGTTAG TGGGAAAATT GAATTGGGCA
      2830       2840       2850       2860       2870       2880
AGTCAGATTT ACCCAGGGAT TAAAGTAAGG CAATTATGTA AACTCCTTAG AGGAACCAAA
      2890       2900       2910       2920       2930       2940
GCACTAACAG AAGTAATACC ACTAACAGAA GAAGCAGAGC TAGAACTGGC AGAAAACAGA
      2950       2960       2970       2980       2990       3000
GAGATTCTAA AAGAACCAGT ACATGGAGTG TATTATGACC CATCAAAAGA CTTAATAGCA
      3010       3020       3030       3040       3050       3060
GAAATACAGA AGCAGGGGCA AGGCCAATGG ACATATCAAA TTTATCAAGA GCCATTTAAA
      3070       3080       3090       3100       3110       3120
AATCTGAAAA CAGGAAAATA TGCAAGAACG AGGGGTGCCC ACACTAATGA TGTAAAACAA
      3130       3140       3150       3160       3170       3180
TTAACAGAGG CAGTGCAAAA AATAACCACA GAAAGCATAG TAATATGGGG AAAGACTCCT
      3190       3200       3210       3220       3230       3240
AAATTTAAAC TACCCATACA AAAGGAAACA TGGGAAACAT GGTGGACAGA GTATTGGCAA
      3250       3260       3270       3280       3290       3300
GCCACCTGGA TTCCTGAGTG GGAGTTTGTC AATACCCCTC CTTTAGTGAA ATTATGGTAC
      3310       3320       3330       3340       3350       3360
CAGTTAGAGA AAGAACCCAT AGTAGGAGCA GAAACGTTCT ATGTAGATGG GGCAGCTAGC
      3370       3380       3390       3400       3410       3420
AGGGAGACTA AATTAGGAAA AGCAGGATAT GTTACTAATA GAGGAAGACA AAAAGTTGTC
      3430       3440       3450       3460       3470       3480
ACCCTAACTG ACACAACAAA TCAGAAGACT GAGTTACAAG CAATTCATCT AGCTTTGCAG
      3490       3500       3510       3520       3530       3540
GATTCGGGAT TAGAAGTAAA TATAGTAACA GACTCACAAT ATGCATTAGG AATCATTCAA
      3550       3560       3570       3580       3590       3600
GCACAACCAG ATAAAAGTGA ATCAGAGTTA GTCAATCAAA TAATAGAGCA GTTAATAAAA
      3610       3620       3630       3640       3650       3660
```

*FIG. 21*

| | | | | | |
|---|---|---|---|---|---|
| AAGCAAAAGG | TCTATCTGGC | ATGGGTACCA | GCACACAAAG | GAATTGGAGG | AAATGAACAA |
| 3670 | 3680 | 3690 | 3700 | 3710 | 3720 |
| GTAGATAAAT | TAGTCAGTGC | TGGAATCAGG | AAAGTACTAT | TTTTAGATGG | AATAGATAAG |
| 3730 | 3740 | 3750 | 3760 | 3770 | 3780 |
| GCCCAAGATG | AACATGAGAA | ATATCACAGT | AATTGGAGAG | CAATGGCTAG | TGATTTTAAC |
| 3790 | 3800 | 3810 | 3820 | 3830 | 3840 |
| CTGCCACCTG | TAGTAGCAAA | AGAAATAGTA | GCCAGCTGTG | ATAAATGTCA | GCTAAAAGGA |
| 3850 | 3860 | 3870 | 3880 | 3890 | 3900 |
| GAAGCCATGC | ATGGACAAGT | AGACTGTAGT | CCAGGAATAT | GGCAACTAGA | TTGTACACAT |
| 3910 | 3920 | 3930 | 3940 | 3950 | 3960 |
| TTAGAAGGAA | AAGTTATCCT | GGTAGCAGTT | CATGTAGCCA | GTGGATATAT | AGAAGCAGAA |
| 3970 | 3980 | 3990 | 4000 | 4010 | 4020 |
| GTTATTCCAG | CAGAAACAGG | GCAGGAAACA | GCATACTTTC | TTTTAAAATT | AGCAGGAAGA |
| 4030 | 4040 | 4050 | 4060 | 4070 | 4080 |
| TGGCCAGTAA | AAACAATACA | TACAGACAAT | GGCAGCAATT | TCACCAGTAC | TACGGTTAAG |
| 4090 | 4100 | 4110 | 4120 | 4130 | 4140 |
| GCCGCCTGTT | GGTGGGCGGG | AATCAAGCAG | GAATTTGGAA | TTCCCTACAA | TCCCCAAAGT |
| 4150 | 4160 | 4170 | 4180 | 4190 | 4200 |
| CAAGGAGTAG | TAGAATCTAT | GAATAAAGAA | TTAAAGAAAA | TTATAGGCCA | GGTAAGAGAT |
| 4210 | 4220 | 4230 | 4240 | 4250 | 4260 |
| CAGGCTGAAC | ATCTTAAGAC | AGCAGTACAA | ATGGCAGTAT | TCATCCACAA | TTTTAAAAGA |
| 4270 | 4280 | 4290 | 4300 | 4310 | 4320 |
| AAAGGGGGGA | TTGGGGGGTA | CAGTGCAGGG | GAAAGAATAG | TAGACATAAT | AGCAACAGAC |
| 4330 | 4340 | 4350 | 4360 | 4370 | 4380 |
| ATACAAACTA | AAGAATTACA | AAAACAAATT | ACAAAAATTC | AAAATTTTCG | GGTTTATTAC |
| 4390 | 4400 | 4410 | 4420 | 4430 | 4440 |
| AGGGACAGCA | GAGATCCACT | TTGGAAAGGA | CCAGCAAAGC | TCCTCTGGAA | AGGTGAAGGG |
| 4450 | 4460 | 4470 | 4480 | 4490 | 4500 |
| GCAGTAGTAA | TACAAGATAA | TAGTGACATA | AAAGTAGTGC | CAAGAAGAAA | AGCAAAGATC |
| 4510 | 4520 | 4530 | 4540 | 4550 | 4560 |
| ATTAGGGATT | ATGGAAAACA | GATGGCAGGT | GATGATTGTG | TGGCAAGTAG | ACAGGATGAG |
| 4570 | 4580 | 4590 | 4600 | 4610 | 4620 |
| GATTAGAACA | TGGAAAAGTT | TAGTAAAACA | CCATATGTAT | GTTTCAGGGA | AAGCTAGGGG |
| 4630 | 4640 | 4650 | 4660 | 4670 | 4680 |
| ATGGTTTTAT | AGACATCACT | ATGAAAGCCC | TCATCCAAGA | ATAAGTTCAG | AAGTACACAT |
| 4690 | 4700 | 4710 | 4720 | 4730 | 4740 |
| CCCACTAGGG | GATGCTAGAT | TGGTAATAAC | AACATATTGG | GGTCTGCATA | CAGGAGAAAG |
| 4750 | 4760 | 4770 | 4780 | 4790 | 4800 |
| AGACTGGCAT | CTGGGTCAGG | GAGTCTCCAT | AGAATGGAGG | AAAAAGAGAT | ATAGCACACA |
| 4810 | 4820 | 4830 | 4840 | 4850 | 4860 |
| AGTAGACCCT | GAACTAGCAG | ACCAACTAAT | TCATCTGTAT | TACTTTGACT | GTTTTTCAGA |
| 4870 | 4880 | 4890 | 4900 | 4910 | 4920 |

FIG. 22

CTCTGCTATA AGAAAGGCCT TATTAGGACA TATAGTTAGC CCTAGGTGTG AATATCAAGC
4930 4940 4950 4960 2970 2980
AGGACATAAC AAGGTAGGAT CTCTACAATA CTTGGCACTA GCAGCATTAA TAACACCAAA
4990 5000 5010 5020 5030 5040
AAAGATAAAG CCACCTTTGC CTAGTGTTAC GAAACTGACA GAGGATAGAT GGAACAAGCC
5050 5060 5070 5080 5090 5100
CCAGAAGACC AAGGGCCACA GAGGGAGCCA CACAATGAAT GGACACTAGA GCTTTTAGAG
5110 5120 5130 5140 5150 5160
GAGCTTAAGA ATGAAGCTGT TAGACATTTT CCTAGGATTT GGCTCCATGG CTTAGGGCAA
5170 5180 5190 5200 5210 5220
CATATCTATG AAACTTATGG GGATACTTGG GCAGGAGTGG AAGCCATAAT AAGAATTCTG
5230 5240 5250 5260 5270 5280
CAACAACTGC TGTTTATCCA TTTCAGAATT GGGTGTCGAC ATAGCAGAAT AGGCGTTACT
5290 5300 5310 5320 5330 5340
CAACAGAGGA GAGCAAGAAA TGGAGCCAGT AGATCCTAGA CTAGAGCCCT GGAAGCATCC
5350 5360 5370 5380 5390 5400
AGGAAGTCAG CCTAAAACTG CTTGTACCAC TTGCTATTGT AAAAAGTGTT GCTTTCATTG
5410 5420 5430 5440 5450 5460
CCAAGTTTGT TTCACAACAA AAGCCTTAGG CATCTCCTAT GGCAGGAAGA AGCGGAGACA
5470 5480 5490 5500 5510 5520
GCGACGAAGA CCTCCTCAAG GCAGTCAGAC TCATCAAGTT TCTCTATCAA AGCAGTAAGT
5530 5540 5550 5560 5570 5580
AGTACATGTA ATGCAACCTA TACAAATAGC AATAGCAGCA TTAGTAGTAG CAATAATAAT
5590 5600 5610 5620 5630 5640
AGCAATAGTT GTGTGGTCCA TAGTAATCAT AGAATATAGG AAAATATTAA GACAAAGAAA
5650 5660 5670 5680 5690 5700
AATAGACAGG TTAATTGATA GACTAATAGA AAGAGCAGAA GACAGTGGCA ATGAGAGTGA
5710 5720 5730 5740 5750 5760
AGGAGAAATA TCAGCACTTG TGGAGATGGG GGTGGAAATG GGGCACCATG CTCCTTGGGA
5770 5780 5790 5800 5810 5820
TATTGATGAT CTGTAGTGCT ACAGAAAAAT TGTGGGTCAC AGTCTATTAT GGGGTACCTG
5830 5840 5850 5860 5870 5880
TGTGGAAGGA AGCAACCACC ACTCTATTTT GTGCATCAGA TGCTAAAGCA TATGATACAG
5890 5900 5910 5920 5930 5940
AGGTACATAA TGTTTGGGCC ACACATGCCT GTGTACCCAC AGACCCCAAC CCACAAGAAG
5950 5960 5970 5980 5990 6000
TAGTATTGGT AAATGTGACA GAAAATTTTA ACATGTGGAA AAATGACATG GTAGAACAGA
6010 6020 6030 6040 6050 6060
TGCATGAGGA TATAATCAGT TTATGGGATC AAAGCCTAAA GCCATGTGTA AAATTAACCC
6070 6080 6090 6100 6110 6120
CACTCTGTGT TAGTTTAAAG TGCACTGATT TGGGGAATGC TACTAATACC AATAGTAGTA
6130 6140 6150 6160 6170 6180

*FIG. 23*

```
ATACCAATAG TAGTAGCGGG GAAATGATGA TGGAGAAAGG AGAGATAAAA AACTGCTCTT
      6190       6200       6210       6220       6230       6240
TCAATATCAG CACAAGCATA AGAGGTAAGG TGCAGAAAGA ATATGCATTT TTTTATAAAC
      6250       6260       6270       6280       6290       6300
TTGATATAAT ACCAATAGAT AATGATACTA CCAGCTATAC GTTGACAAGT TGTAACACCT
      6310       6320       6330       6340       6350       6360
CAGTCATTAC ACAGGCCTGT CCAAAGGTAT CCTTTGAGCC AATTCCCATA CATTATTGTG
      6370       6380       6390       6400       6410       6420
CCCCGGCTGG TTTTGCGATT CTAAAATGTA ATAATAAGAC GTTCAATGGA ACAGGACCAT
      6430       6440       6450       6460       6470       6480
GTACAAATGT CAGCACAGTA CAATGTACAC ATGGAATTAG GCCAGTAGTA TCAACTCAAC
      6490       6500       6510       6520       6530       6540
TGCTGTTGAA TGGCAGTCTA GCAGAAGAAG AGGTAGTAAT TAGATCTGCC AATTTCACAG
      6550       6560       6570       6580       6590       6600
ACAATGCTAA AACCATAATA GTACAGCTGA ACCAATCTGT AGAAATTAAT TGTACAAGAC
      6610       6620       6630       6640       6650       6660
CCAACAACAA TACAAGAAAA AGTATCCGTA TCCAGAGGGG ACCAGGGAGA GCATTTGTTA
      6670       6680       6690       6700       6710       6720
CAATAGGAAA AATAGGAAAT ATGAGACAAG CACATTGTAA CATTAGTAGA GCAAAATGGA
      6730       6740       6750       6760       6770       6780
ATGCCACTTT AAAACAGATA GCTAGCAAAT TAAGAGAACA ATTTGGAAAT AATAAAACAA
      6790       6800       6810       6820       6830       6840
TAATCTTTAA GCAATCCTCA GGAGGGGACC CAGAAATTGT AACGCACAGT TTTAATTGTG
      6850       6860       6870       6880       6890       6900
GAGGGGAATT TTTCTACTGT AATTCAACAC AACTGTTTAA TAGTACTTGG TTTAATAGTA
      6910       6920       6930       6940       6950       6960
CTTGGAGTAC TGAAGGGTCA AATAACACTG AAGGAAGTGA CACAATCACA CTCCCATGCA
      6970       6980       6990       7000       7010       7020
GAATAAAACA ATTTATAAAC ATGTGGCAGG AAGTAGGAAA AGCAATGTAT GCCCCTCCCA
      7030       7040       7050       7060       7070       7080
TCAGCGGACA AATTAGATGT TCATCAAATA TTACAGGGCT GCTATTAACA AGAGATGGTG
      7090       7100       7110       7120       7130       7140
GTAATAACAA CAATGGGTCC GAGATCTTCA GACCTGGAGG AGGAGATATG AGGGACAATT
      7150       7160       7170       7180       7190       7200
GGAGAAGTGA ATTATATAAA TATAAAGTAG TAAAAATTGA ACCATTAGGA GTAGCACCCA
      7210       7220       7230       7240       7250       7260
CCAAGGCAAA GAGAAGAGTG GTGCAGAGAG AAAAAAGAGC AGTGGGAATA GGAGCTTTGT
      7270       7280       7290       7300       7310       7320
TCCTTGGGTT CTTGGGAGCA GCAGGAAGCA CTATGGGCGC ACGGTCAATG ACGCTGACGG
      7390       7340       7350       7360       7370       7380
TACAGGCCAG ACAATTATTG TCTGGTATAG TGCAGCAGCA GAACAATTTG CTGAGGGCTA
      7390       7400       7410       7420       7430       7440
```

FIG. 24

TTGAGGCGCA ACAGCATCTG TTGCAACTCA CAGTCTGGGG CATCAAGCAG CTCCAGGCAA
7450 7460 7470 7480 7490 7500
GAATCCTGGC TGTGGAAAGA TACCTAAAGG ATCAACAGCT CCTGGGGATT TGGGGTTGCT
7510 7520 7530 7540 7550 7560
CTGGAAAACT CATTTGCACC ACTGCTGTGC CTTGGAATGC TAGTTGGAGT AATAAATCTC
7570 7580 7590 7600 7610 7620
TGGAACAGAT TTGGAATAAC ATGACCTGGA TGGAGTGGGA CAGAGAAATT AACAATTACA
7630 7640 7650 7660 7670 7680
CAAGCTTAAT ACATTCCTTA ATTGAAGAAT CGCAAAACCA GCAAGAAAAG AATGAACAAG
7690 7700 7710 7720 7730 7740
AATTATTGGA ATTAGATAAA TGGGCAAGTT TGTGGAATTG GTTTAACATA ACAAATTGGC
7750 7760 7770 7780 7790 7800
TGTGGTATAT AAAAATATTC ATAATGATAG TAGGAGGCTT GCTAGGTTTA AGAATAGTTT
7810 7800 7810 7820 7830 7840
TTGCTGTACT TTCTATAGTG AATAGAGTTA GGCAGGGATA TTCACCATTA TCGTTTCAGA
7870 7880 7890 7900 7910 7920
CCCACCTCCC AACCCCGAGG GGACCCGACA GGCCCGAAGG AATAGAAGAA GAAGGTGGAG
7930 7940 7950 7960 7970 7980
AGAGAGACAG AGACAGATCC ATTCGATTAG TGAACGGATC CTTAGCACTT ATCTGGGACG
7990 8000 8010 8020 8030 8040
ATCTGCGGAG CCTTGTGCCT CTTCAGCTAC CACCGCTTGA GAGACTTACT CTTGATTGTA
8050 8060 8070 8080 8090 8100
ACGAGGATTG TGGAACTTCT GGGACGCAGG GGGTGGGAAG CCCTCAAATA TTGGTGGAAT
8110 8120 8130 8140 8150 8160
CTCCTACAGT ATTGGAGTCA GGAACTAAAG AATAGTGCTG TTAGCTTGCT CAATGCCACA
8170 8180 8190 8200 8210 8220
GCCATAGCAG TAGCTGAGGG GACAGATAGG GTTATAGAAG TAGTACAAGG AGCTTGTAGA
8230 8240 8250 8260 8270 8280
GCTATTCGCC ACATACCTAG AAGAATAAGA CAGGGCTTGG AAAGGATTTT GCTATAAGAT
8290 8300 8310 8320 8330 8340
GGGTGGCAAG TGGTCAAAAA GTAGTGTGGT TGGATGGCCT ACTGTAAGGG AAAGAATGAG
8350 8360 8370 8380 8390 8400
ACGAGCTGAG CCAGCAGCAG ATGGGGTGGG AGCAGCATCT CGAGACCTGG AAAAACATGG
8410 8420 8430 8440 8450 8460
AGCAATCACA AGTAGCAATA CAGCAGCTAC CAATGCTGCT TGTGCCTGGC TAGAAGCACA
8470 8480 8490 8500 8510 8520
AGAGGAGGAG GAGGTGGGTT TTCCAGTCAC ACCTCAGGTA CCTTTAAGAC CAATGACTTA
8530 8540 8550 8560 8570 8580
CAAGGCAGCT GTAGATCTTA GCCACTTTTT AAAAGAAAAG GGGGGACTGG AAGGGCTAAT
8590 8600 8610 8620 8630 8640
TCACTCCCAA CGAAGACAAG ATATCCTTGA TCTGTGGATC TACCACACAC AAGGCTACTT
8650 8660 8670 8680 8690 8700

*FIG. 25*

| | | | | | |
|---|---|---|---|---|---|
| CCCTGATTGG | CAGAACTACA | CACCAGGGCC | AGGGGTCAGA | TATCCACTGA | CCTTTGGATG |
| 8710 | 8720 | 8730 | 8740 | 8750 | 8760 |
| GTGCTACAAG | CTAGTACCAG | TTGAGCCAGA | TAAGGTAGAA | GAGGCCAATA | AAGGAGAGAA |
| 8770 | 8780 | 8790 | 8800 | 8810 | 8820 |
| CACCAGCTTG | TTACACCCTG | TGAGCCTGCA | TGGAATGGAT | GACCCTGAGA | GAGAAGTGTT |
| 8830 | 8840 | 8850 | 8860 | 8870 | 8880 |
| AGAGTGGAGG | TTTGACAGCC | GCCTAGCATT | TCATCACGTG | GCCCGAGAGC | TGCATCCGGA |
| 8890 | 8900 | 8910 | 8920 | 8930 | 8940 |
| GTACTTCAAG | AACTGCTGAC | ATCGAGCTTG | CTACAAGGGA | CTTTCCGCTG | GGGACTTTCC |
| 8950 | 8960 | 8970 | 8980 | 8990 | 9000 |
| AGGGAGGCGT | GGCCTGGGCG | GAACTGGGGA | GTGGCGAGCC | CTCAGATGCT | GCATATAAGC |
| 9010 | 9020 | 9030 | 9040 | 9050 | 9060 |
| AGCTGCTTTT | TGCCTGTACT | GGGTCTCTCT | GGTTAGACCA | GATTTGAGCC | TGGGAGCTCT |
| 9070 | 9080 | 9090 | 9100 | 9110 | 9120 |
| CTGGCTAACT | AGGGAACCCA | CTGCTTAAGC | CTCAATAAAG | CTT | |

*FIG. 26*

DNA SEQUENCES AND PEPTIDES OF HUMAN IMMUNODEFICIENCY VIRUS (HIV-1)

This application is a continuation of application Ser. No. 07/953,060, filed Nov. 5, 1992, which is a division of application Ser. No. 07/158,652, filed Feb. 22, 1988, which is a division of application Ser. No. 06/771,248, filed Aug. 30, 1985.

This invention relates to cloned DNA sequences indistinguishable from genomic RNA and DNA of lymphadenopathy-associated virus (LAV), a process for their preparation and their uses. It relates more particularly to stable probes including a DNA sequence which can be used for the detection of the LAV virus or related viruses or DNA proviruses in any medium, particularly biological samples containing any of them. The invention also relates to polypeptides, whether glycosylated or not, encoded by said DNA sequences.

Lymphadenopathy-associated virus (LAV) is a human retrovirus first isolated from the lymph node of a homosexual patient with lymphadenopathy syndrome, frequently a prodrome or a benign form of acquired immune deficiency syndrome (AIDS). Subsequently, other LAV isolates were recovered from patients with AIDS or pre-AIDS. All available data are consistent with the virus being the causative agent of AIDS.

A method for cloning such DNA sequences has already been disclosed in British Patent Application Nr. 84 23659, filed on Sep. 19, 1984. Reference is hereafter made to that application as concerns subject matter in common with the further improvements to the invention disclosed herein.

SUMMARY OF THE INVENTION

The present invention aims at providing additional new means which are not only useful for the detection of LAV or related viruses, (hereafter more generally referred to as "LAV viruses" or "Human Immunodeficiency Virus Type 1" or simply "HIV-1", but also new means that have more versatility, particularly in detecting specific parts of the genomic RNA of said viruses whose expression products are not always directly detectable by immunological methods.

The present invention further aims at providing polypeptides containing sequences in common with polypeptides encoded by the LAV genomic RNA. It relates even more particularly to polypeptides comprising antigenic determinants included in the proteins encoded and expressed by the LAV genome occuring in nature. An additional object of the invention is to further provide means for the detection of proteins related to LAV virus, particularly for the diagnosis of AIDS or pre-AIDS or, to the contrary, for the detection of antibodies against the LAV virus or proteins related therewith, particularly in patients afflicted with AIDS or pre-AIDS or more generally in asymtomatic carriers and in blood-related products. Finally, the invention also aims at providing immunogenic polypeptides, and more particularly protective polypeptides for use in the preparation of vaccine compositions against AIDS or related syndromes.

The present invention relates to additional DNA fragments, hybridizable with the genomic RNA of LAV as they will be disclosed hereafter, as well as with additional cDNA variants corresponding to the whole genomes of LAV viruses. It further relates to DNA recombinants containing said DNAs or cDNA fragments.

The invention relates more particularly to a cDNA variant corresponding to the whole of LAV retroviral genomes, which is characterized by a series of restriction sites in the order hereafter (from the 5' end to the 3' end).

The coordinates of the successive sites of the whole LAV genome (restriction map) are indicated hereafter too, with respect to the Hind III site (selected as of coordinate 1) which is located in the R region. The coordinates are estimated with an accuracy of ±200 bp:

| | |
|---|---|
| Hind III | 0 |
| Sac I | 50 |
| Hind III | 520 |
| Pst I | 800 |
| Hind III | 1100 |
| Bgl II | 1500 |
| Kpn I | 3500 |
| Kpn I | 3900 |
| Eco RI | 4100 |
| Eco RI | 5300 |
| Sal I | 5500 |
| Kpn I | 6100 |
| Bgl II | 6500 |
| Bgl II | 7600 |
| Hind III | 7850 |
| Bam HI | 8150 |
| Xho I | 8600 |
| Kpn I | 8700 |
| Bgl II | 8750 |
| Bgl II | 9150 |
| Sac I | 9200 |
| Hind III | 9250 |

Another DNA variant according to this invention optionally contains an additional Hind III approximately at the 5 550 coordinate.

Reference is further made to FIG. 1 which shows a more detailed restriction map of said whole DNA (λJ19).

An even more detailed nucleotide sequence of a preferred DNA according to the invention is shown in FIGS. 4–12 hereafter.

The invention further relates to other preferred DNA fragments which will be referred to hereafter.

BRIEF DESCRIPTION OF THE DRAWINGS

Additional features of the invention will appear in the course of the non-limitative disclosure of additional features of preferred DNAs of the invention, as well as of preferred polypeptides according to the invention. Reference will further be had to the drawings in which:

FIGS. 4–12 show the successive nucleotide sequences of a complete LAV genome. The possible peptide sequences in relation to the three possible reading phases related to the nucleotide sequences shown are also indicated;

FIGS. 13–18 reiterate the sequence of part of the LAV genome containing the genes coding for the envelope proteins, with particular boxed peptide sequences which correspond to groups which normally carry glycosyl groups.

FIGS. 19–26 reiterate the DNA sequence of the LAV genome.

DETAILED DESCRIPTION OF PREFERRED EMBODIMENTS

Figure 1:
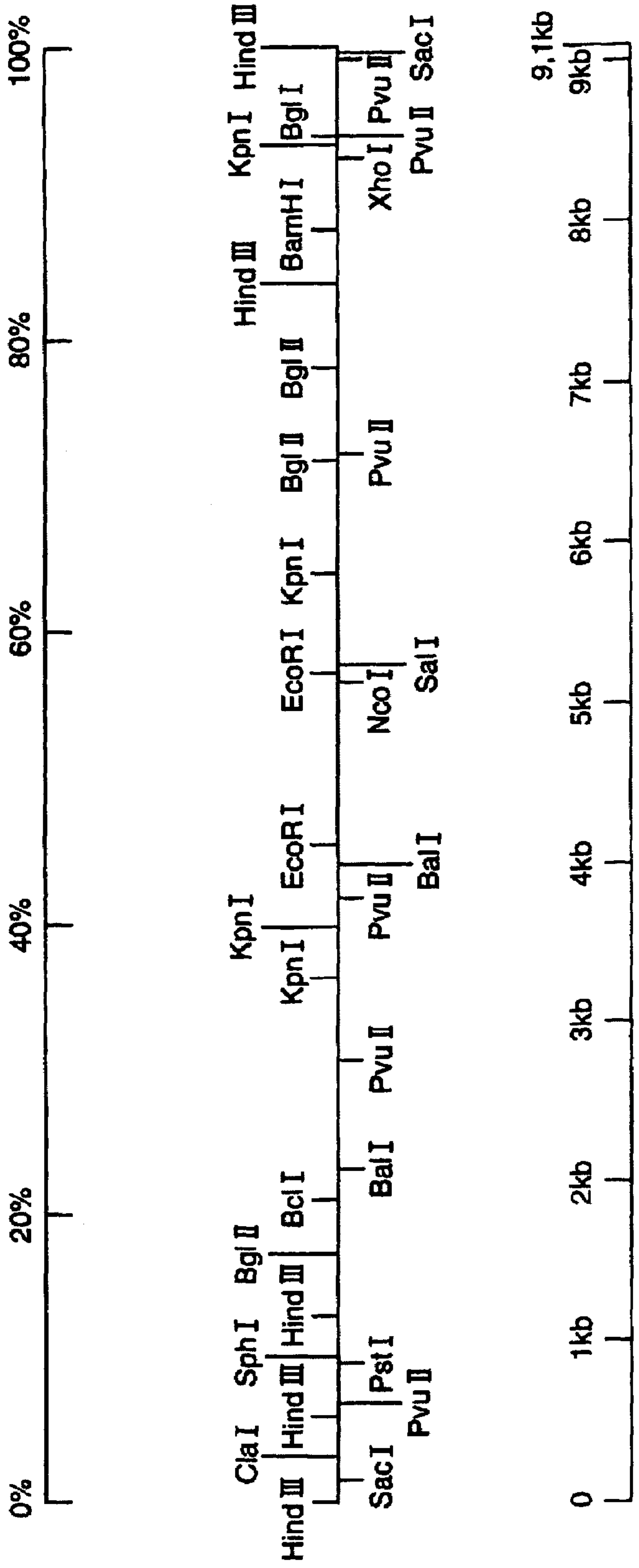
FIG. 1 is the restriction map of a complete LAV genome (clone λJ19)

The sequencing and determination of sites of particular interest were carried out on a phage recombinant corresponding to λJ19 disclosed in the abovesaid British Patent Application Nr. 84 23659. A method for preparing it is disclosed in that application.

The whole recombinant phage DNA of clone λJ19 (disclosed in the earlier application) was sonicated according to the protocol of DEININGER (1983), Analytical Biochem. 129, 218. The DNA was repaired by a Klenow reaction for 12 hours at 16° C. The DNA was electrophoresed through 0.8 Z agarose gel and DNA in the size range of 300–600 bp was cut out and electroeluted and precipitated. Resuspended DNA (in 10 mM Tris, pH 8; 0.1 mM EDTA) was ligated into M13mp8 RF DNA (cut by the restriction enzyme SmaI and subsequently alkaline phosphated), using T4 DNA- and RNA-ligases (Maniatis et al (1982)—Molecular cloning—Cold Spring Harbor Laboratory). An *E. coli* strain designated as TG1 was used for further study. This strain has the following genotype:

Δlac pro, supE, thi.$F^-$traD36, proAB, lac$I^q$, ZΔM15.$r^-$

This *E. coli* TGI strain has the peculiarity of enabling recombinants to be recognized easily. The blue colour of the cells transfected with plasmids which did not recombine with a fragment of LAV DNA is not modified. To the contrary cells transfected by a recombinant plasmid containing a LAV DNA fragment yield white colonies. The technique which was used is disclosed in Gene (1983), 26, 101.

This strain was transformed with the ligation mix using the Hanahan method (Hanahan D (1983) J. Mol. Biol. 166, 557). Cells were plated out on tryptone-agarose plate with IPTG and X-gal in soft agarose. White plaques were either picked and screened or screened directly in situ using nitrocellulose filters. Their DNAs were hybridized with nick-translated DNA inserts of pUC18 Hind III subclones of λJ19. This permitted the isolation of the plasmids or subclones of λ which are identified in the table hereafter. In relation to this table it should also be noted that the designation of each plasmid is followed by the deposition number of a cell culture of *E. coli* TGI containing the corresponding plasmid at the "Collection Nationale des Cultures de Micro-organismes" (C.N.C.M.) of the Pasteur Institute in Paris, France. A non-transformed TGI cell line was also deposited at the C.N.C.M. under Nr. I-364. All these deposits took place on Nov. 15, 1984. The sizes of the corresponding inserts derived from the LAV genome have also been indicated.

TABLE

| Essential features of the recombinant plasmids | | |
|---|---|---|
| pJ19 - 1 plasmid | (I-365) | 0.5 kb |
| Hind III - Sac I - Hind III | | |
| pJ19 - 17 plasmid | (I-367) | 0.6 kb |
| Hind III - Pst 1 - Hind III | | |
| pJ19 - 6 plasmid | (I-366) | 1.5 kb |
| Hind III (5') | | |
| Bam HI | | |
| Xho I | | |
| Kpn I | | |
| Bgl II | | |
| Sac I (3') | | |
| Hind III | | |
| pJ19 - 13 plasmid | (I-368) | 6.7 kb |
| Hind III (5') | | |
| Bgl II | | |
| Kpn I | | |
| Kpn I | | |
| Eco RI | | |
| Eco RI | | |
| Sal I | | |
| Kpn I | | |
| Bgl II | | |
| Bgl II | | |
| Hind III (3') | | |

Positively hybridizing M13 phage plates were grown up for 5 hours and the single-stranded DNAs were extracted.

M13mp8 subclones of λJ19 DNAs were sequenced according to the dideoxy method and technology devised by Sanger et al. Sanger et al (1977), Proc. Natl. Acad. Sci. USA, 74, 5463 and M13 cloning and sequencing handbook, AMERSHAM (1983). The 17-mer oligonucleotide primer α-$^{35}$SdATP (400 Ci/mmol, AMERSHAM), and 0.5×–5× buffer gradient gels (Biggen M. D. et al (1983), Proc. Natl. Acad. Sci. USA, 50, 3963) were used. Gels were read and put into the computer under the programs of Staden (Staden R. (1982), Nucl. Acids Res. 10, 4731). All the appropriate references and methods can be found in the AMERSHAM M13 cloning and sequencing handbook.

The complete sequence of λJ19 was deduced from the experiments as further disclosed hereafter.

FIGS. 4–12 provide the DNA nucleotide sequence of the complete genome of LAV. The numbering of the nucleotides starts from a left most Hind III restriction site (5' AAG . . . ) of the restriction map. The numbering occurs in tens whereby the last zero number of each of the numbers occurring on the drawings is located just below the nucleotide corresponding to the nucleotides designated. That is, the nucleotide at position 10 is T, the nucleotide at position 20 is C, etc.

Above each of the lines of the successive nucleotide sequences there are provided three lines of single letters corresponding to the amino acid sequence deduced from the DNA sequence (using the genetic code) for each of the three reading phases, whereby said single letters have the following meanings:

| | |
|---|---|
| A: | alanine |
| R: | arginine |
| K: | lysine |
| H: | histidine |
| C: | cysteine |
| M: | methionine |
| W: | tryptophan |
| F: | phenylalanine |
| Y: | tyrosine |
| L: | leucine |
| V: | valine |
| I: | isoleucine |
| G: | glycine |
| T: | threonine |
| S: | serine |
| E: | glutamic acid |
| O: | Aspartic acid |
| N: | asparagine |
| Q: | glutamine |
| P: | proline. |

The asterik signs "*" correspond to stop codons (i.e. TAA, TAG and TGA).

Figure 4:
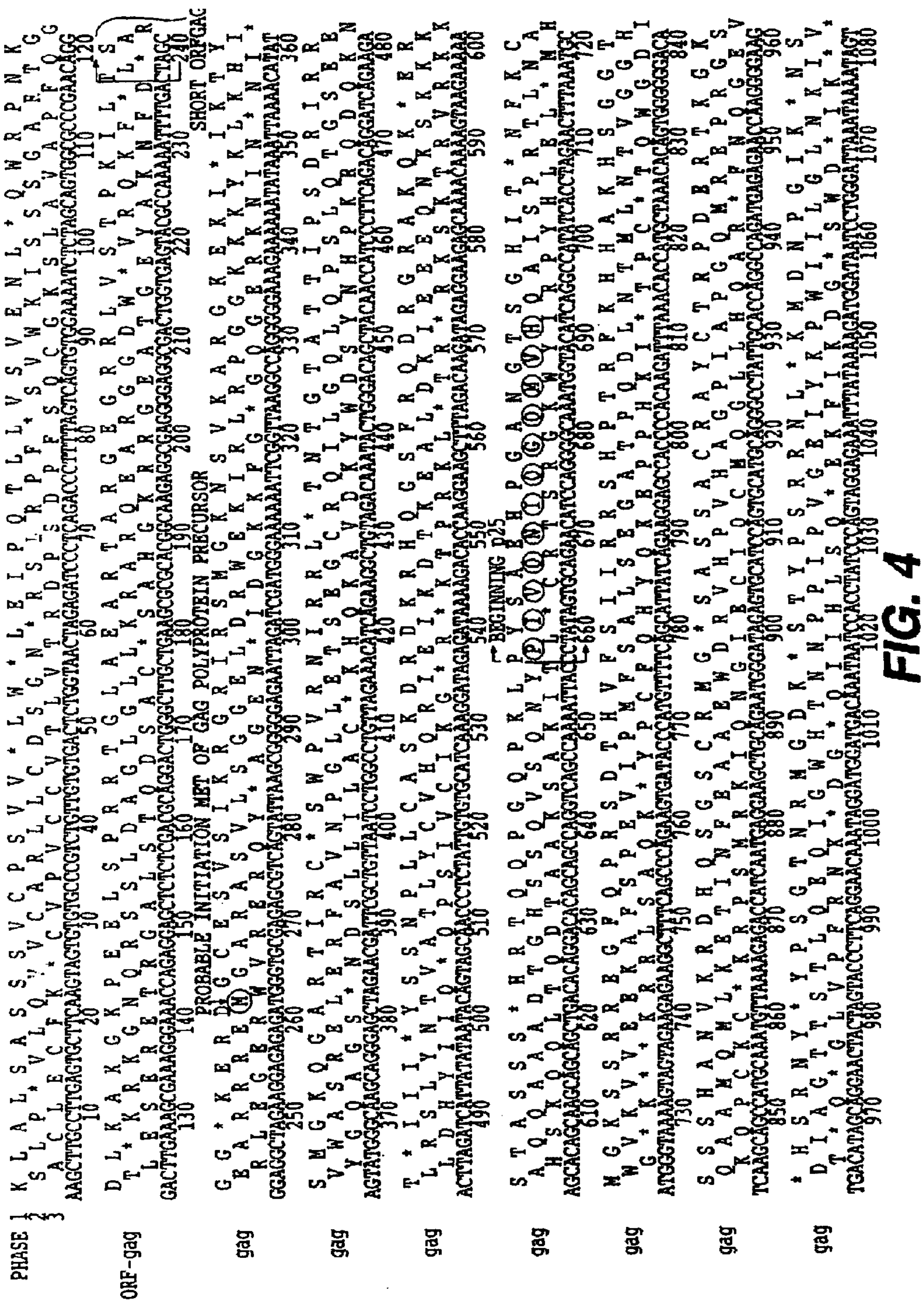
Figure 5:
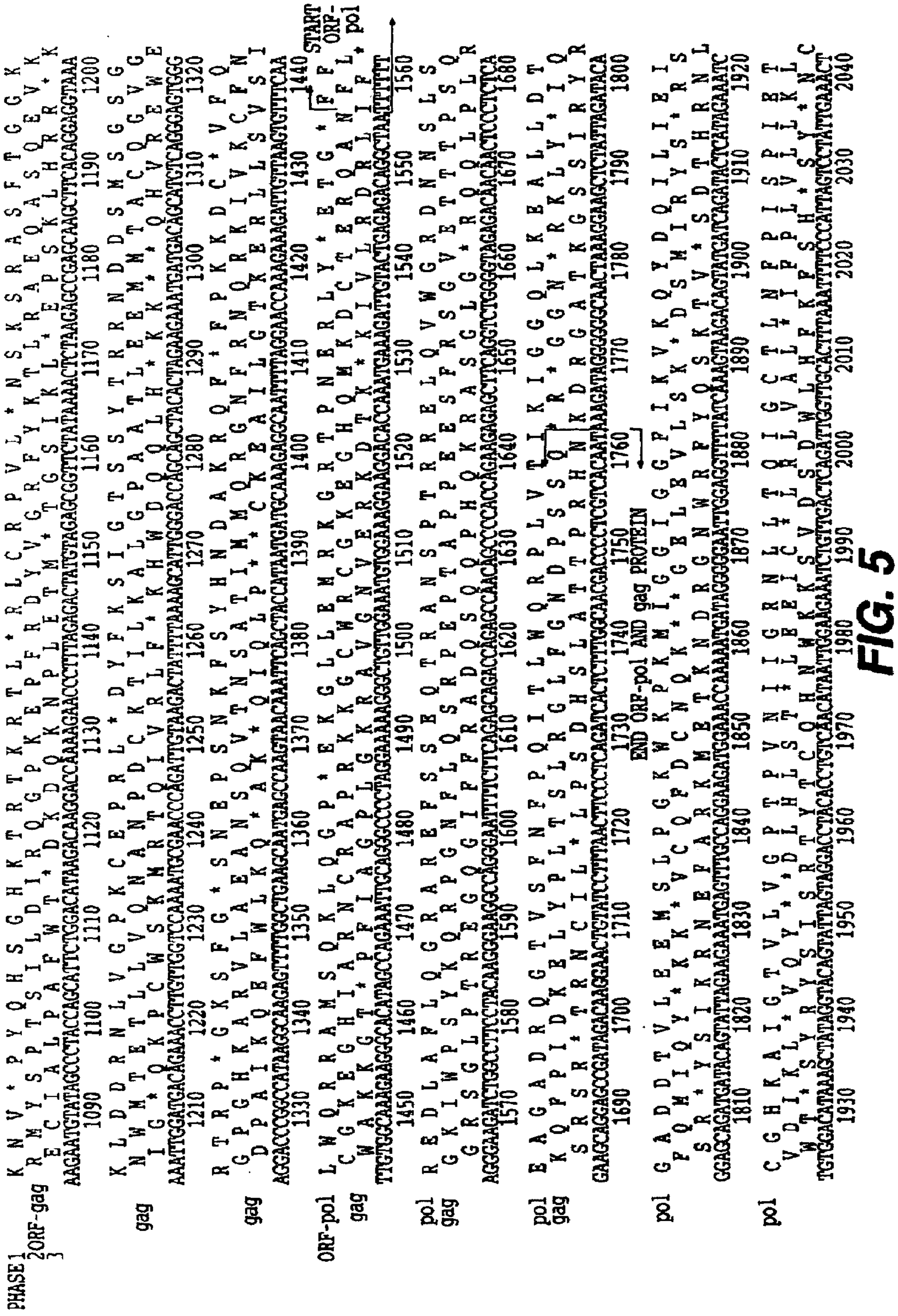
Figure 6:
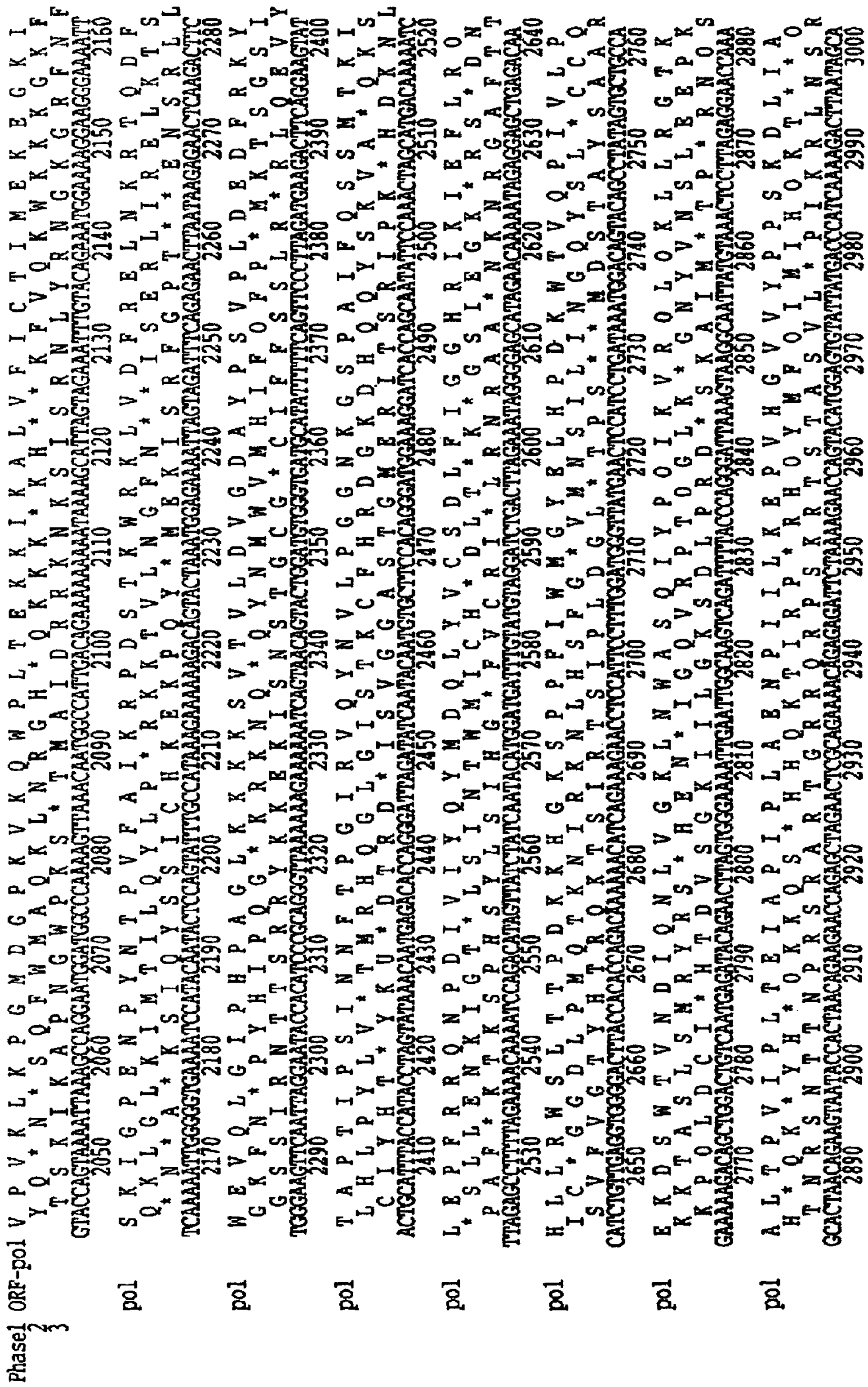
Figure 7:
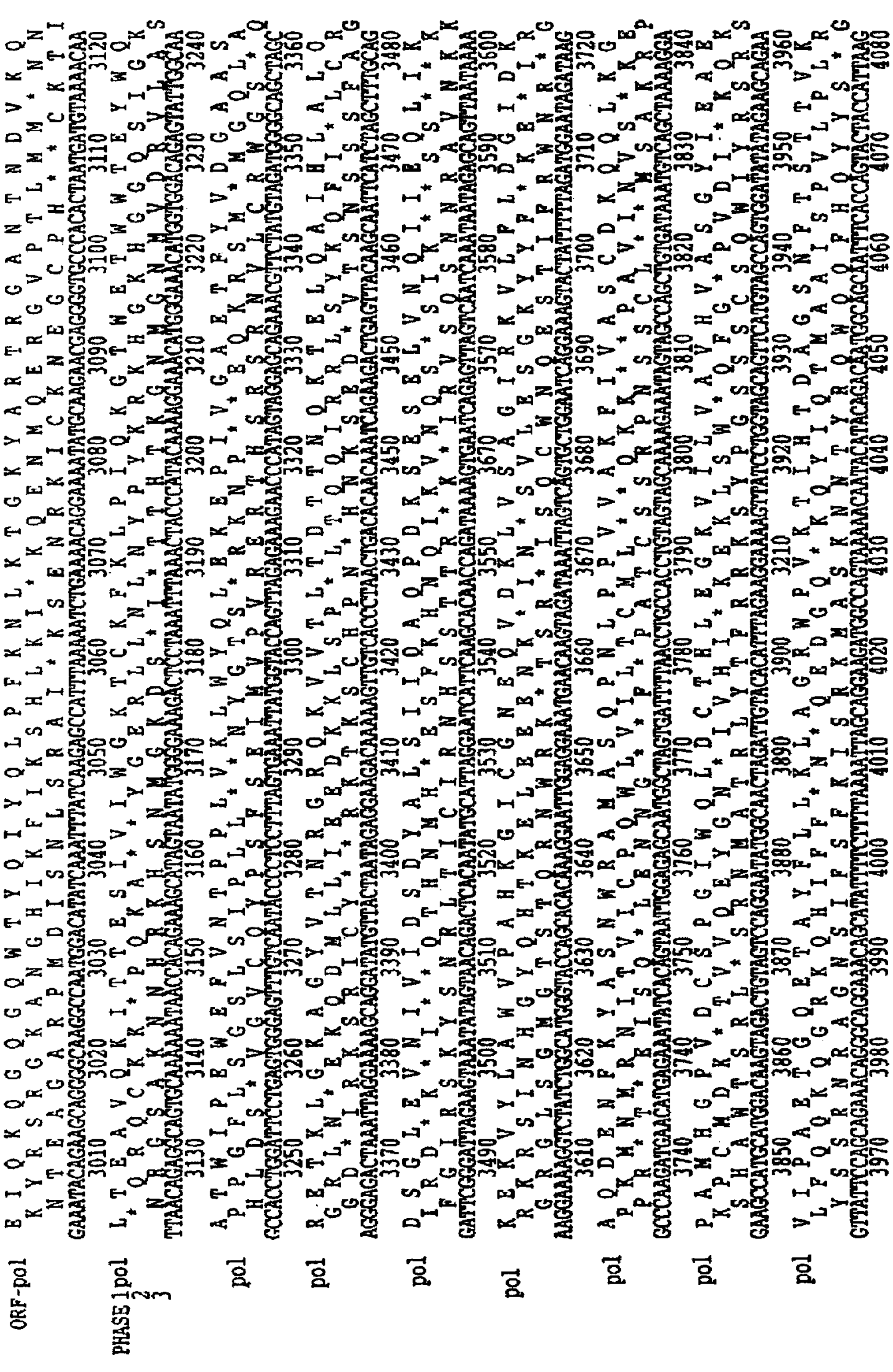
Figure 8:
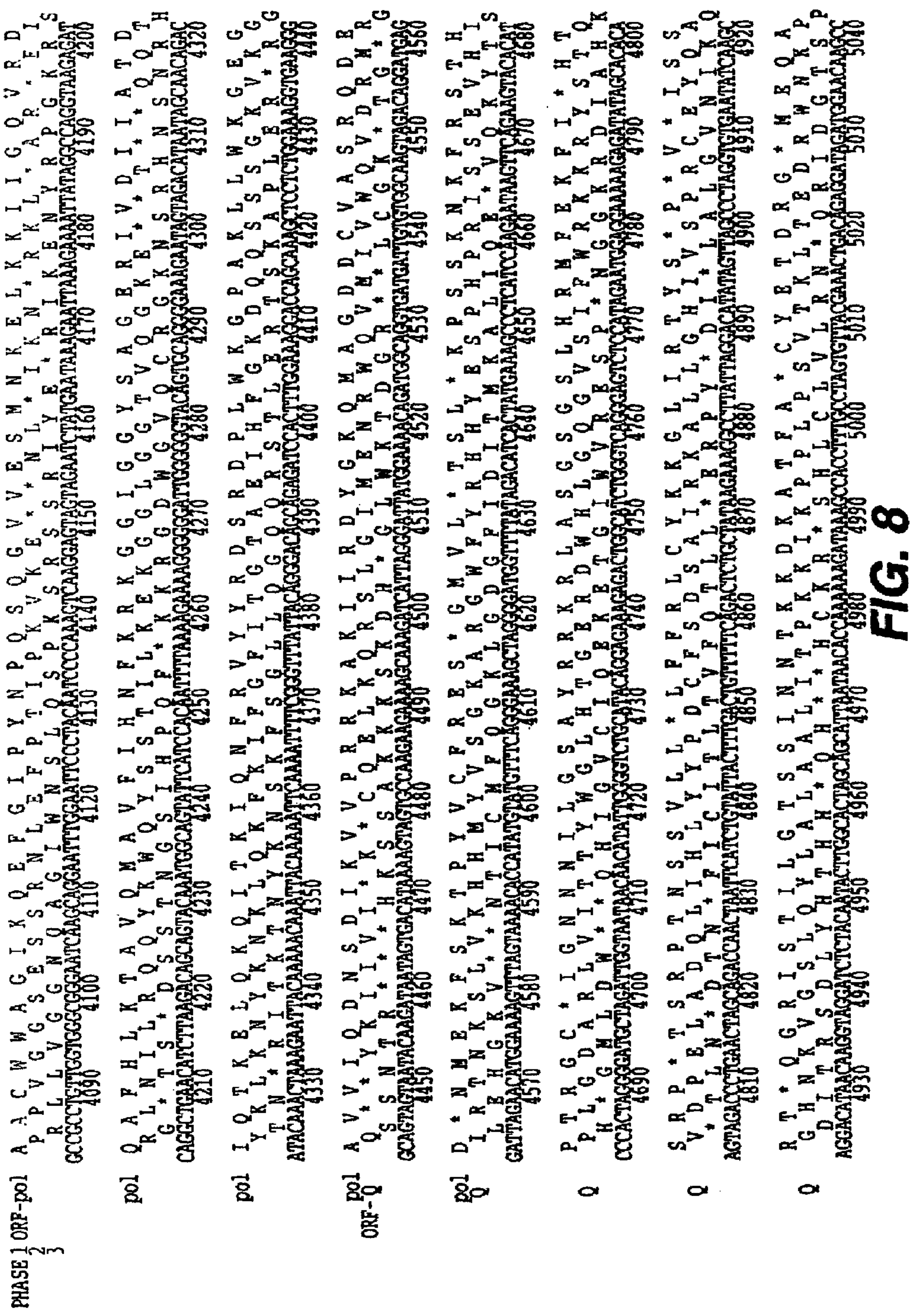
Figure 9:
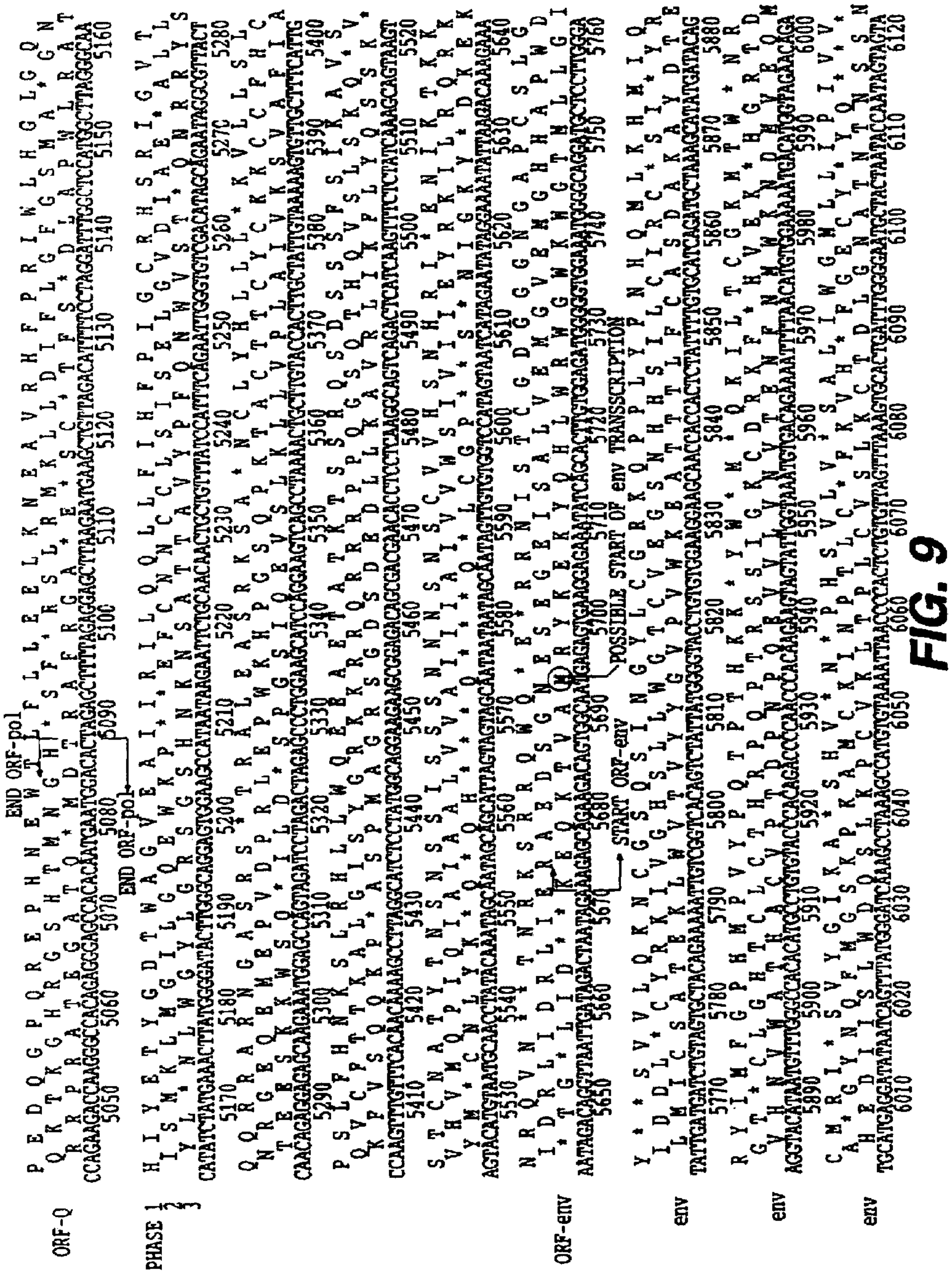
Figure 10:
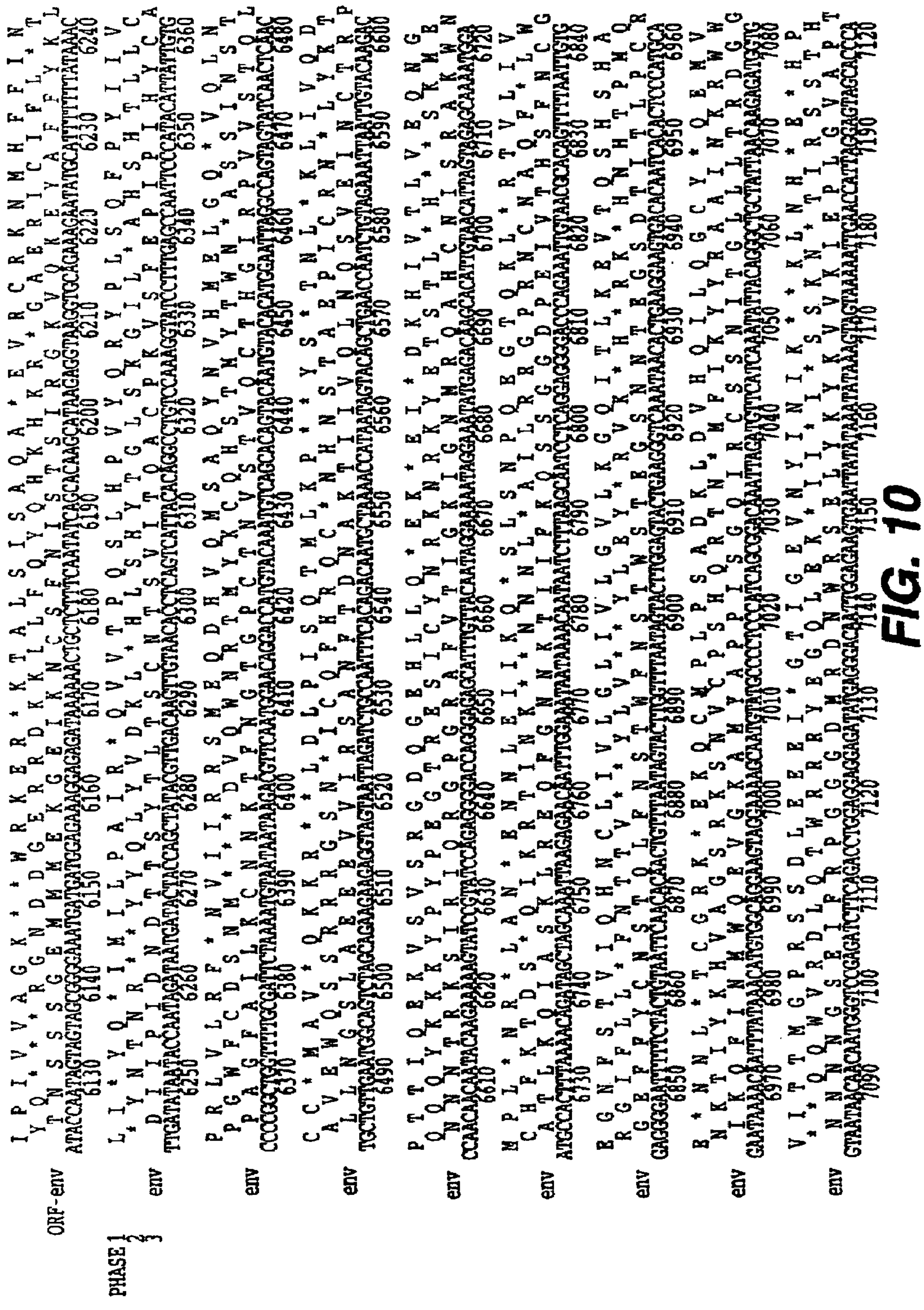
Figure 11:
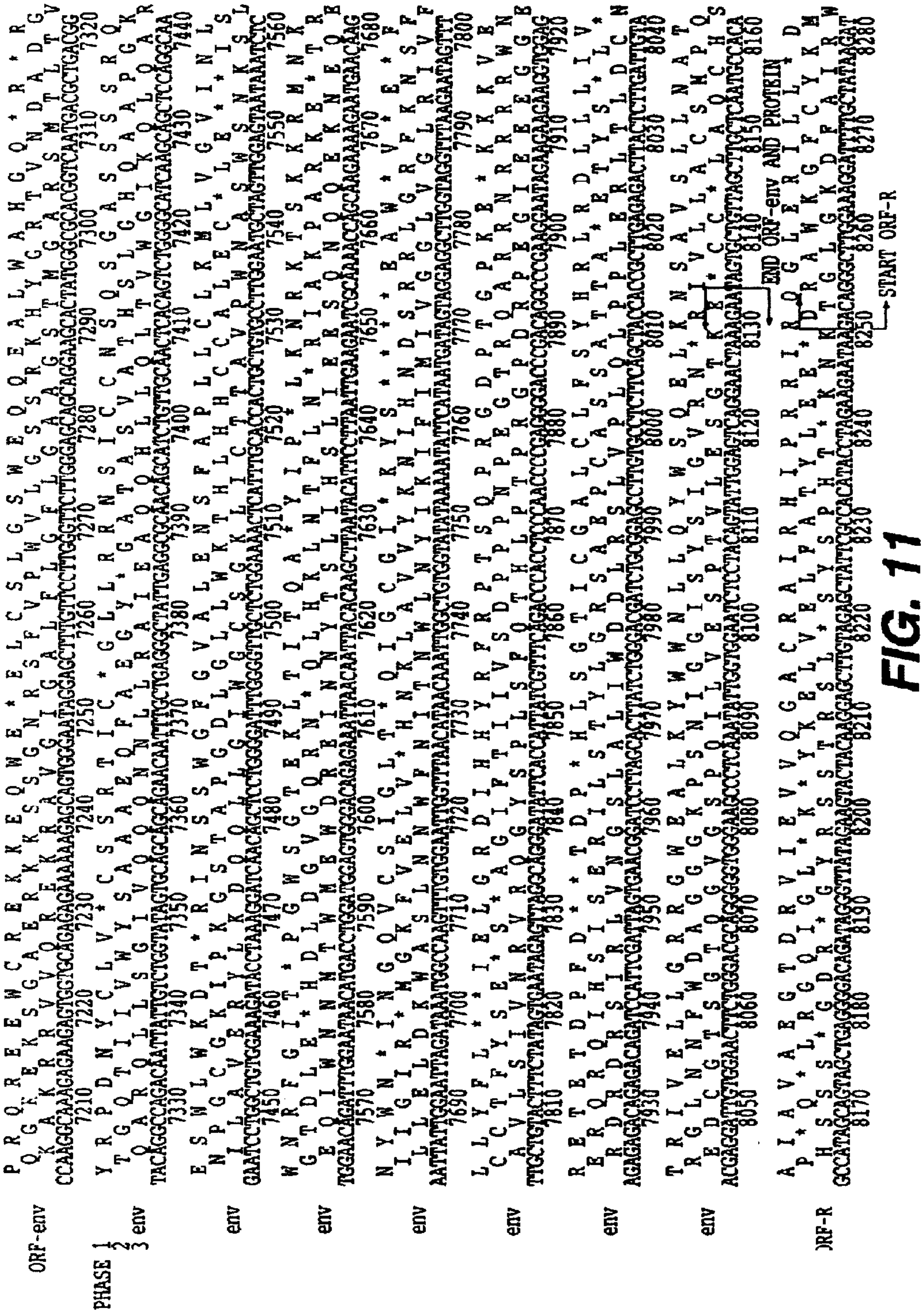

Starting above the first line of the DNA nucleotide sequence of FIG. 4, the three reading phases are respectively marked "1", "2", "3", on the left handside of the drawing. The same relative presentation of the three theoretical reading phases is then used over all the successive lines of the LAV nucleotide sequence.

Figure 2:
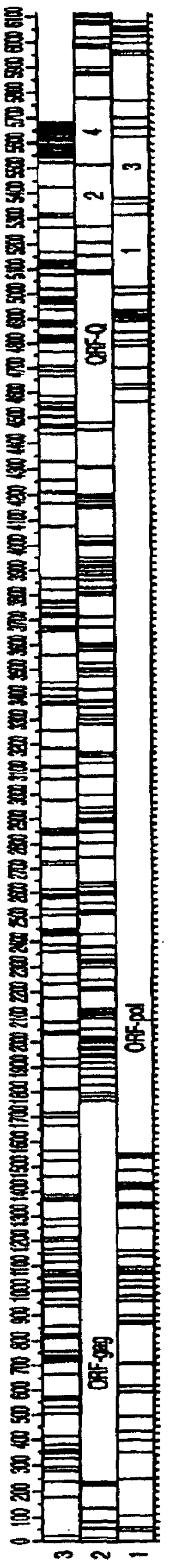
FIGS. 2 and 3 show diagrammatically parts of the three possible reading phases of LAV genomic RNA, including the open reading frames (ORF) apparent in each of said reading phases.
Figure 3:
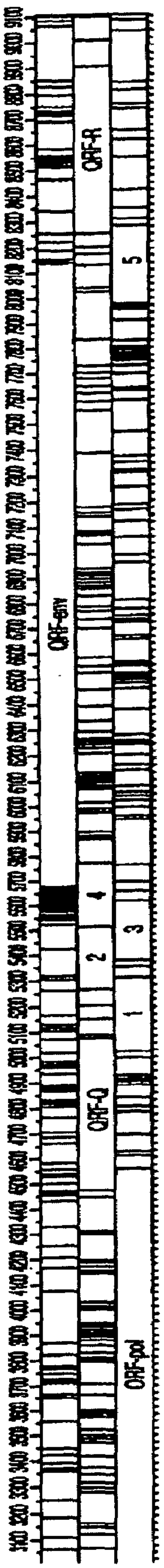

FIGS. 2 and 3 provides a diagrammatized representation of the lengths of the successive open reading frames corresponding to the successive reading phases (also referred to by numbers "1", "2" and "3" appearing in the left handside part of FIG. 2. The relative positions of these open reading frames (ORF) with respect to the nucleotide structure of the LAV genome is referred to by the scale of numbers representative of the respective positions of the corresponding nucleotides in the DNA sequence. The vertical bars correspond to the positions of the corresponding stop codons.

1) The "gag gene" (or ORF-gag)

The "gag gene" codes for core proteins. Particularly it appears that a genomic fragment (ORF-gag) thought to code for the core antigens including the p25, p18 and p13 proteins is located between nucleotide position 236 (starting with 5' CTA GCG GAG 3') and nucleotide position 1759 (ending by CTCG TCA CAA 3'). The structure of the peptides or proteins encoded by parts of said ORF is deemed to be that corresponding to phase 2.

The methionine amino acid "M" coded by the ATG at position 260–262 is the probable initiation methionine of the gag protein precursor. The end of ORF-gag and accordingly of gag protein appears to be located at position 1759.

The beginning of p25 protein thought to start by a P-I-V-Q-N-I-Q-G-Q-M-V-M . . . amino acid sequence is thought to be coded for by the nucleotide sequence CCTATA . . . , starting at position 656.

Hydrophilic peptides in the gag open reading frame are identified hereafter. They are defined starting from amino acid 1=Met (M) coded by the ATG starting from 260-2 in the LAV DNA sequence.

Those hydrophilic peptides are

| | | |
|---|---|---|
| 12–32 | amino acids | inclusive |
| 37–46 | " | " |
| 49–79 | " | " |
| 88–153 | " | " |
| 158–165 | " | " |
| 178–188 | " | " |
| 200–220 | " | " |
| 226–234 | " | " |
| 239–264 | " | " |
| 288–331 | " | " |
| 352–361 | " | " |
| 377–390 | " | " |
| 399–432 | " | " |
| 437–484 | " | " |
| 492–498 | " | " |

The invention also relates to any combination of these peptides.

2) The "pol gene" (or ORF-pol)

FIGS. 4–12 also show that the DNA fragments extending from nucleotide position 1555 (starting with 5'TTT TTT . . . 3' to nucleotide position 5086 is thought to correspond to the pol gene. The polypeptidic structure of the corresponding polypeptides is deemed to be that corresponding to phase 1. It stops at position 4563 (and by 5'G GAT GAG GAT 3').

These genes are thought to code for the virus polymerase or reverse transcriptase.

3) The envelope gene (or ORF-env)

The DNA sequence thought to code for envelope proteins is thought to extend from nucleotide position 5670 (starting with 5'AAA GAG GAG A . . . 3') up to nucleotide position 8132 (ending by . . . A ACT AAA GAA 3'). Polypeptide structures of sequences of the envelope protein correspond to those read according to the "phase 3" reading phase.

The start of env transcription is thought to be at the level of the ATG codon at positions 5691–5693.

Additional features of the envelope protein coded by the env genes appear on FIGS. 13–18. These are to be considered as paired FIGS. 13 and 14; 15 and 16; 17 and 18, respectively.

It is to be mentioned that because of format difficulties

FIG. 14 overlaps to some extent with FIG. 13,

FIG. 16 overlaps to some extent with FIG. 15,

FIG. 18 overlaps to some extent with FIG. 17.

Thus, for instance FIGS. 13 and 14 must be considered together. Particularly the sequence shown on the first line on the top of FIG. 13 overlaps with the sequence shown on the first line on the top of FIG. 14. In other words, the starting of the reading of the successive sequences of the env gene as represented in FIGS. 13–18 involves first reading the first line at the top of FIG. 13 then proceeding further with the first line of FIG. 14. One then returns to the beginning of the second line of FIG. 13, then again further proceed with the reading of the second line of page 14, etc. The same observations then apply to the reading of the paired FIGS. 15 and 16, and paired FIGS. 17 and 18, respectively.

The locations of neutralizing epitopes are further apparent in FIGS. 13–18. Reference is more particularly made to the boxed groups of three letters included in the amino acid sequences of the envelope proteins (reading phase 3) which can be designated generally by the formula N-X-S or N-X-T, wherein X is any other possible amino acid. Thus, the initial protein product of the env gene is a glycoprotein of molecular weight in excess of 91,000. These groups are deemed to generally carry glycosylated groups. These N-X-S and N-X-T groups with attached glycosylated groups form together hydrophilic regions of the protein and are deemed to be located at the periphery of and to be exposed outwardly with respect to the normal conformation of the proteins. Consequently, they are considered as being epitopes which can efficiently be brought into play in vaccine compositions.

The invention thus concerns with more particularity peptide sequences included in the env proteins and excizable therefrom (or having the same amino acid structure), having sizes not exceeding 200 amino acid.

Preferred peptides of this invention (referred to hereafter as a, b, c, d, e, f, are deemed to correspond to those encoded by the nucleotide sequences which extend, respectively, between the following positions:

| | | | | |
|---|---|---|---|---|
| a) | from about | 6095 | to about | 6200 |
| b) | " | 6260 | " | 6310 |
| c) | " | 6390 | " | 6440 |
| d) | " | 6485 | " | 6620 |
| e) | " | 6860 | " | 6930 |
| f) | " | 7535 | " | 7630 |

Other hydrophilic peptides in the env open reading frame are identified hereafter. They are defined starting from amino acid 1=lysine (K) coded by the AAA at position 5670-2 in the LAV DNA sequence.

These hydrophilic peptides are

| | | |
|---|---|---|
| 8–23 | amino acids | inclusive |
| 63–78 | " | " |
| 82–90 | " | " |
| 97–123 | " | " |
| 127–183 | " | " |
| 197–201 | " | " |
| 239–294 | " | " |
| 300–327 | " | " |
| 334–381 | " | " |
| 397–424 | " | " |
| 466–500 | " | " |
| 510–523 | " | " |
| 551–577 | " | " |
| 594–603 | " | " |
| 621–630 | " | " |
| 657–679 | " | " |
| 719–758 | " | " |
| 780–803 | " | " |

The invention also relates to any combination of these peptides.

4) The other ORF

The invention further concerns DNA sequences which provide open reading frames defined as ORF-Q, ORF-R and as "1", "2", "3", "4", "5", the relative position of which appears more particularly in FIGS. 2 and 3.

These ORFs have the following locations:

| | | | |
|---|---|---|---|
| ORF-Q | phase 1 | start 4478 | stop 5086 |
| ORF-R | phase 2 | start 8249 | stop 8896 |
| ORF-1 | phase 1 | start 5029 | stop 5316 |
| ORF-2 | phase 2 | start 5273 | stop 5515 |
| ORF-3 | phase 1 | start 5383 | stop 5616 |
| ORF-4 | phase 2 | start 5519 | stop 5773 |
| ORF-5 | phase 1 | start 7966 | stop 8279 |

The LTR (long terminal repeats) can be defined as lying between position 8560 and position 160 (and extending over position 9097/1). As a matter of fact the end of the genome is at 9097 and, because of the LTR structure of the retrovirus, links up with the beginning of the sequence:

```
          Hind III
CTCAATAAAGCTTG CTTG
        /|
       / |
   9097  1
```

The invention concerns more particularly all the DNA fragments which have been more specifically referred to hereabove and which correspond to open reading frames. It will be understood that the man skilled in the art will be able to obtain them all, for instance by cleaving an entire DNA corresponding to the complete genome of a LAV species, such as by cleavage by a partial or complete digestion thereof with a suitable restriction enzyme and by the subsequent recovery of the relevant fragments. The different DNAs disclosed in the earlier mentioned British Application can be resorted to also as a source of suitable fragments. The techniques disclosed hereabove for the isolation of the fragments which were then included in the plasmids referred to hereabove and which were then used for the DNA sequencing can be used.

Of course other methods can be used. Some of them have been exemplified in the earlier British Application. Reference is for instance made to the following methods.

a) DNA can be transfected into mammalian cells with appropriate selection markers by a variety of techniques, such as calcium phosphate precipitation, polyethylene glycol, protoplast-fusion, etc.

b) DNA fragments corresponding to genes can be cloned into expression vectors for *E. coli,* yeast or mammalian cells and the resultant proteins purified.

c) The proviral DNA can be "shot-gunned" (fragmented), into procaryotic expression vectors to generate fusion polypeptides. Recombinants producing antigenically competent fusion proteins can be identified by simply screening the recombinants with antibodies against LAV antigens.

The invention also relates more specifically to cloned probes which can be made starting from any DNA fragment according to this invention, thus to recombinant DNAs containing such fragments, particularly any plasmids amplifiable in procaryotic or eucaryotic cells and carrying said fragments.

Using the cloned DNA fragments as a molecular hybridization probe—either by marking with radionucleotides or with fluorescent reagents—LAV virion RNA may be detected directly in the blood, body fluids and blood products (e.g. of the antihemophilic factors, such as Factor VIII concentrates) and vaccines, i.e. hepatitis 8 vaccine. It has already been shown that whole virus can be detected in culture supernatants of LAV producing cells. A suitable method for achieving that detection comprises immobilizing virus onto a support, e.g. nitrocellulose filters, etc., disrupting the virion, and hybridizing with labelled (radiolabelled or "cold" fluorescent- or enzyme-labelled) probes. Such an approach has already been developed for Hepatitis 8 virus in peripheral blood (according to SCOTTO J. et al. Hepatology (1983), 3, 379–384).

Probes according to the invention can also be used for rapid screening of genomic DNA derived from the tissue of patients with LAV related symptoms to see if the proviral DNA or RNA is present in host tissue and other tissues.

A method which can be used for such screening comprises the following steps: extraction of DNA from tissue, restriction enzyme cleavage of said DNA, electrophoresis of the fragments and Southern blotting of genomic DNA from tissues, and subsequent hybridization with labelled cloned LAV proviral DNA. Hybridization in situ can also be used.

Lymphatic fluids and tissues and other non-lymphatic tissues of humans, primates and other mammalian species can also be screened to see if other evolutionary related retrovirus exist. The methods referred to hereabove can be used, although hybridization and washings would be done under non-stringent conditions.

The DNA according to the invention can also be used for achieving the expression of LAV viral antigens for diagnostic purposes.

The invention also relates to the polypeptides themselves which can be expressed by the different DNAs of the inventions, particularly by the ORFs or fragments thereof, in appropriate hosts, particularly procaryotic or eucaryotic hosts, after transformation thereof with a suitable vector previously modified by the corresponding DNAs.

These polypeptides can be used as diagnostic tools, particularly for the detection of antibodies in biological media, particularly in sera or tissues of persons afflicted with pre-AIDS or AIDS, or simply carrying antibodies in the absence of any apparent disorders. Conversely, the different peptides according to this invention can be used themselves for the production of antibodies, preferably monoclonal antibodies specific of the different peptides respectively. For the production of hybridomas secreting said monoclonal antibodies, conventional production and screening methods are used. These monoclonal antibodies, which themselves are part of the invention, than provide very useful tools for the identification and even determination of relative properties of the different polypeptides or proteins in biological samples, particularly human samples containing LAV or related viruses.

Thus, all of the above peptides can be used in diagnostics as sources of immunogens or antigens free of viral particles, produced using non-permissive systems, and thus of little or no biohazzard risk.

The invention further relates to the hosts (procaryotic or eucaryotic cells) which are transformed by the above-mentioned recombinants and which are capable of expressing said DNA fragments.

Finally, it also relates to vaccine compositions whose active principle is to be constituted by any of the expressed antigens, i.e. whole antigens, fusion polypeptides or oligopeptides, in association with a suitable pharmaceutically or physiologically acceptable carrier.

Preferably, the active principles to be considered in that field consist of the peptides containing less than 250 amino acid units, preferably less than 150 as deducible from the complete genomes of LAV, and even more preferably those peptides which contain one or more groups selected from N-X-S and N-X-T as defined above. Preferred peptides for use in the production of vaccinating principles are peptides (a) to (f) as defined above. By way of example having no limitative character, there may be mentioned that suitable dosages of the vaccine compositions are those which enable administration to the host, particularly human host, ranging from 10 to 500 micrograms per kg, for instance 50 to 100 micrograms per kg.

For the purpose of clarity, FIGS. 19 to 26 are added. Reference may be made thereto in case of difficulties of reading blurred parts of FIGS. 4 to 12.

Needless to say that FIGS. 19–26 are merely a reiteration of the whole DNA sequence of the LAV genome.

Finally, the invention also concerns vectors for the transformation of eucaryotic cells of human origin, particularly lymphocytes, the polymerases of which are capable of recognizing the LTRs of LAV. Particularly, said vectors are characterized by the presence of a LAV LTR therein, said LTR being then active as a promoter enabling the efficient transcription and translation in a suitable host of the above defined DNA insert coding for a determined protein placed under its controls.

Needless to say that the invention extends to all variants of genomes and corresponding DNA fragments (ORFs) having substantially equivalent properties, all of said genomes belonging to retroviruses which can be considered as equivalents of LAV.

The invention claimed is:

1. A nucleic acid of ORF-R of Human Immunodeficiency Virus Type 1 (HIV-1) comprising the sequence:

```
8250       8260       8270       8280       8290
  GA CAGGGCTTGG AAAGGATTTT GCTATAAGAT GGGTGGCAAG

      8300       8310       8320       8330
TGGTCAAAAA GTAGTGTGGT TGGATGGCCT ACTGTAAGGG

      8340       8350       8360       8370
```

-continued

```
AAAGAATGAG ACGAGCTGAG CCAGCAGCAG ATGGGGTGGG

      8380       8390       8400       8410
AGCAGCATCT CGAGACCTGG AAAAACATGG AGCAATCACA

      8420       8430       8440       8450
AGTAGCAATA CAGCAGCTAC CAATGCTGCT TGTGCCTGGC

      8460       8470       8480       8490
TAGAAGCACA AGAGGAGGAG GAGGTGGGTT TTCCAGTCAC

      8500       8510       8520       8530
ACCTCAGGTA CCTTTAAGAC CAATGACTTA CAAGGCAGCT

      8540       8550       8560       8570
GTAGATCTTA GCCACTTTTT AAAAGAAAAG GGGGGACTGG

      8580       8590       8600       8610
AAGGGCTAAT TCACTCCCAA CGAAGACAAG ATATCCTTGA

      8620       8630       8640       8650
TCTGTGGATC TACCACACAC AAGGCTACTT CCCTGATTGG

      8660       8670       8680       8690
CAGAACTACA CACCAGGGCC AGGGGTCAGA TATCCACTGA

      8700       8710       8720       8730
CCTTTGGATG GTGCTACAAG CTAGTACCAG TTGAGCCAGA

      8740       8750       8760       8770
TAAGGTAGAA GAGGCCAATA AAGGAGAGAA CACCAGCTTG

      8780       8790       8800       8810
TTACACCCTG TGAGCCTGCA TGGAATGGAT AGAGTGGAGG

      8820       8830       8840       8850
TTTGACAGCC GCCTAGCATT TCATCACGTG GCCCGAGAGC

      8860       8870       8890       8900
TCATCACGTG GCCCGAGAGC TGCATCCGGA GTACTTCAAG

AACTGC,
```

wherein the nucleic acid is in a eukaryotic expression vector that expresses a protein comprising the amino acid sequence:

MGGKWSKSSVVGWPTVRERMR-RAEPAADGVGAASRDLEKHGAITSSNTAAT NAA-CAWLEAQEEEEVGFPVTPQVPLRPMTY-KAAVDLSHFLKEKGGLEGLIHSQRRQDI LDLWIYHTQGYFPDWQNYTPGPGVRY-PLTFGWCYKLVPVEPDKVEEANKGENTSLLH PVSL-HGMDDPEREVLEWRFDSRLAFHHVAREL-HPEYFKNC.

2. The nucleic acid of claim 1, wherein the nucleic acid is in a mammalian expression vector.

3. A nucleic acid of ORF-R of Human Immunodeficiency Virus Type 1 (HIV-1) comprising the sequence:

```
8250       8260       8270       8280       8290       8300
  GA CAGGGCTTGG AAAGGATTTT GCTATAAGAT GGGTGGCAAG TGGTCAAAAA

      8310       8320       8330       8340       8350
GTAGTGTGGT TGGATGGCCT ACTGTAAGGG AAAGAATGAG ACGAGCTGAG

      8360       8370       8380       8390       8400
CCAGCAGCAG ATGGGGTGGG AGCAGCATCT CGAGACCTGG AAAAACATGG

      8410       8420       8430       8440       8450
AGCAATCACA AGTAGCAATA CAGCAGCTAC CAATGCTGCT TGTGCCTGGC

      8460       8470       8480       8490       8500
TAGAAGCACA AGAGGAGGAG GAGGTGGGTT TTCCAGTCAC ACCTCAGGTA

      8510       8520       8530       8540       8550
CCTTTAAGAC CAATGACTTA CAAGGCAGCT GTAGATCTTA GCCACTTTTT

      8560       8570       8580       8590       8600
AAAAGAAAAG GGGGGACTGG AAGGGCTAAT TCACTCCCAA CGAAGACAAG

      8610       8620       8630       8640       8650
ATATCCTTGA TCTGTGGATC TACCACACAC AAGGCTACTT CCCTGATTGG

      8660       8670       8680       8690       8700
CAGAACTACA CACCAGGGCC AGGGGTCAGA TATCCACTGA CCTTTGGATG

      8710       8720       8730       8740       8750
GTGCTACAAG CTAGTACCAG TTGAGCCAGA TAAGGTAGAA GAGGCCAATA

      8760       8770       8780       8790       8800
AAGGAGAGAA CACCAGCTTG TTACACCCTG TGAGCCTGCA TGGAATGGAT

      8810       8820       8830       8840       8850
GACCCTGAGA GAGAAGTGTT AGAGTGGAGG TTTGACAGCC GCCTAGCATT

      8860       8870       8890       8900
TCATCACGTG GCCCGAGAGC TGCATCCGGA GTACTTCAAG AACTGC,
```

wherein the nucleic acid is in a yeast expression vector that expresses a protein comprising the amino acid sequence:

MGGKWSKSSVVGWPTVRERMR-RAEPAADGVGAASRDLEKHGAITSSNTAAT NAA-CAWLEAQEEEEVGFPVTPQVPLRPMTY-KAAVDLSHFLKEKGGLEGLIHSQRRQDI LDLWIYHTQGYFPDWQNYTPGPGVRY-PLTFGWCYKLVPVEPDKVEEANKGENTSLLH PVSL-HGMDDPEREVLEWRFDSRLAFHHVAREL-HPEYFKNC.

4. A recombinant eukaryotic expression vector comprising a nucleic acid fragment of Human Immunodeficiency Virus Type 1 (HIV-1), wherein the vector expresses a protein comprising the amino acid sequence:

MGGKWSKSSVVGWPTVRERMR-RAEPAADGVGAASRDLEKHGAITSSNTAAT NAA-CAWLEAQEEEEVGFPVTPQVPLRPMTY-KAAVDLSHFLKEKGGLEGLIHSQRRQDI LDLWIYHTQGYFPDWQNYTPGPGVRY-PLTFGWCYKLVPVEPDKVEEANKGENTSLLH PVSL-HGMDDPEREVLEWRFDSRLAFHHVAREL-HPEYFKNC.

5. A recombinant mammalian expression vector comprising a nucleic acid fragment of Human Immunodeficiency Virus Type 1 (HIV-1), wherein the vector expresses a protein comprising the amino acid sequence:

MGGKWSKSSVVGWPTVRERMR-RAEPAADGVGAASRDLEKHGAITSSNTAAT NAA-CAWLEAQEEEEVGFPVTPQVPLRPMTY-KAAVDLSHFLKEKGGLEGLIHSQRRQDI LDLWIYHTQGYFPDWQNYTPGPGVRY-PLTFGWCYKLVPVEPDKVEEANKGENTSLLH PVSL-HGMDDPEREVLEWRFDSRLAFHHVAREL-HPEYFKNC.

6. A recombinant yeast expression vector comprising a nucleic acid fragment of Human Immunodeficiency Virus Type 1 (HIV-1), wherein the vector expresses a protein comprising the amino acid sequence:

MGGKWSKSSVVGWPTVRERMR-RAEPAADGVGAASRDLEKHGAITSSNTAAT NAA-CAWLEAQEEEEVGFPVTPQVPLRPMTY-KAAVDLSHFLKEKGGLEGLIHSQRRQDI LDLWIYHTQGYFPDWQNYTPGPGVRY-PLTFGWCYKLVPVEPDKVEEANKGENTSLLH PVSL-HGMDDPEREVLEWRFDSRLAFHHVAREL-HPEYFKNC.

7. A nucleic acid of ORF-R of Human Immunodeficiency Virus Type 1 (HIV-1) comprising the sequence:

```
8250       8260       8270       8280       8290       8300
  GA CAGGGCTTGG AAAGGATTTT GCTATAAGAT GGGTGGCAAG TGGTCAAAAA

      8310       8320       8330       8340       8350
GTAGTGTGGT TGGATGGCCT ACTGTAAGGG AAAGAATGAG ACGAGCTGAG

      8360       8370       8380       8390       8400
CCAGCAGCAG ATGGGGTGGG AGCAGCATCT CGAGACCTGG AAAAACATGG

      8410       8420       8430       8440       8450
AGCAATCACA AGTAGCAATA CAGCAGCTAC CAATGCTGCT TGTGCCTGGC

      8460       8470       8480       8490       8500
TAGAAGCACA AGAGGAGGAG GAGGTGGGTT TTCCAGTCAC ACCTCAGGTA

      8510       8520       8530       8540       8550
CCTTTAAGAC CAATGACTTA CAAGGCAGCT GTAGATCTTA GCCACTTTTT

      8560       8570       8580       8590       8600
AAAAGAAAAG GGGGGACTGG AAGGGCTAAT TCACTCCCAA CGAAGACAAG

      8610       8620       8630       8640       8650
ATATCCTTGA TCTGTGGATC TACCACACAC AAGGCTACTT CCCTGATTGG

      8660       8670       8680       8690       8700
CAGAACTACA CACCAGGGCC AGGGGTCAGA TATCCACTGA CCTTTGGATG

      8710       8720       8730       8740       8750
GTGCTACAAG CTAGTACCAG TTGAGCCAGA TAAGGTAGAA GAGGCCAATA

      8760       8770       8780       8790       8800
AAGGAGAGAA CACCAGCTTG TTACACCCTG TGAGCCTGCA TGGAATGGAT

      8810       8820       8830       8840       8850
GACCCTGAGA GAGAAGTGTT AGAGTGGAGG TTTGACAGCC GCCTAGCATT

      8860       8870       8890       8900
TCATCACGTG GCCCGAGAGC TGCATCCGGA GTACTTCAAG AACTGC,
```

wherein the sequence is linked to a promoter in a eukaryotic expression vector that allows the expression of a protein comprising the amino acid sequence:

MGGKWSKSSVVGWPTVRERMR-RAEPAADGVGAASRDLEKHGAITSSNTAAT NAA-CAWLEAQEEEEVGFPVTPQVPLRPMTY-KAAVDLSHFLKEKGGLEGLIHSQRRQDI LDLWIYHTQGYFPDWQNYTPGPGVRY-PLTFGWCYKLVPVEPDKVEEANKGENTSLLH PVSL-HGMDDPEREVLEWRFDSRLAFHHVAREL-HPEYFKNC.

8. The nucleic acid of claim 7, wherein the nucleic acid is linked to a promoter in a yeast expression vector.

9. The nucleic acid of claim 7, wherein the nucleic acid is linked to a promoter in a mammalian expression vector.

10. An isolated eukaryotic expression vector that expresses Nef protein of Human Immunodeficiency Virus Type 1 (HIV-1), wherein the sequence hybridizes under stringent conditions to a DNA comprising the sequence:

```
8250       8260       8270       8280       8290       8300
  GA CAGGGCTTGG AAAGGATTTT GCTATAAGAT GGGTGGCAAG TGGTCAAAAA

      8310       8320       8330       8340       8350
GTAGTGTGGT TGGATGGCCT ACTGTAAGGG AAAGAATGAG ACGAGCTGAG

      8360       8370       8380       8390       8400
CCAGCAGCAG ATGGGGTGGG AGCAGCATCT CGAGACCTGG AAAAACATGG

      8410       8420       8430       8440       8450
AGCAATCACA AGTAGCAATA CAGCAGCTAC CAATGCTGCT TGTGCCTGGC

      8460       8470       8480       8490       8500
TAGAAGCACA AGAGGAGGAG GAGGTGGGTT TTCCAGTCAC ACCTCAGGTA

      8510       8520       8530       8540       8550
CCTTTAAGAC CAATGACTTA CAAGGCAGCT GTAGATCTTA GCCACTTTTT

      8560       8570       8580       8590       8600
AAAAGAAAAG GGGGGACTGG AAGGGCTAAT TCACTCCCAA CGAAGACAAG
```

-continued

```
      8610       8620       8630       8640       8650
ATATCCTTGA TCTGTGGATC TACCACACAC AAGGCTACTT CCCTGATTGG

      8660       8670       8680       8690       8700
CAGAACTACA CACCAGGGCC AGGGGTCAGA TATCCACTGA CCTTTGGATG

      8710       8720       8730       8740       8750
GTGCTACAAG CTAGTACCAG TTGAGCCAGA TAAGGTAGAA GAGGCCAATA

      8760       8770       8780       8790       8800
AAGGAGAGAA CACCAGCTTG TTACACCCTG TGAGCCTGCA TGGAATGGAT

      8810       8820       8830       8840       8850
GACCCTGAGA GAGAAGTGTT AGAGTGGAGG TTTGACAGCC GCCTAGCATT

      8860       8870       8890       8900
TCATCACGTG GCCCGAGAGC TGCATCCGGA GTACTTCAAG AACTGC.
```

11. An isolated eukaryotic expression vector that encodes the following amino acid sequence:

MGGKWSKSSVVGWPTVRERMR-RAEPAADGVGAASRDLEKHGAITSSNTAATNAACA WLEAQEEEEVGFPVTPQVPLRPMTY-KAAVDLSHFLKEKGGLEGLIHSQRRQDILDLWI YHTQGYFPDWQNYTPGPGVRYPLTFGW-CYKLVPVEPDKVEEANKGENTSLLHPVSL HGMD-DPEREVLEWRFDSRLAFHHVARELHPEYFKNC.

12. A method of expressing an HIV-1 protein comprising inserting an expression vector of any of claims 4–6, 10, and 11 into a host cell under conditions suitable for the expression of the amino acid sequence.

13. A method of making a eukaryotic expression vector that encodes the following amino acid sequence:

MGGKWSKSSVVGWPTVRERMR-RAEPAADGVGAASRDLEKHGAITSSNTAATNAACA WLEAQEEEEVGFPVTPQVPLRPMTY-KAAVDLSHFLKEKGGLEGLIHSQRRQDILDLWI YHTQGYFPDWQNYTPGPGVRYPLTFGW-CYKLVPVEPDKVEEANKGENTSLLHPVSL HGMD-DPEREVLEWRFDSRLAFHHVARELHPEYFKNC comprising replicating the eukaryotic expression vector in a host cell.

* * * * *

UNITED STATES PATENT AND TRADEMARK OFFICE

CERTIFICATE OF CORRECTION

PATENT NO. : 7,119,181 B1

APPLICATION NO. : 08/308218

DATED : October 10, 2006

INVENTOR(S) : Marc Alizon et al.

It is certified that error appears in the above-identified patent and that said Letters Patent is hereby corrected as shown below:

Claim 1, col. 10, in the sequence listing (lines 42-45),

“ 8810 8820 8830 8840
AGAGTGGAGG TTTGACAGCC GCCTAGCATT TCATCACGTG
8850
GCCCGAGAGC”

should read

-- 8810 8820 8830 8840
GACCCTGAGA GAGAAGTGTT AGAGTGGAGG TTTGACAGCC
8850
GCCTAGCATT--

Signed and Sealed this

Twenty-sixth Day of December, 2006

JON W. DUDAS
*Director of the United States Patent and Trademark Office*